US008604080B2

(12) United States Patent
Cleveland

(10) Patent No.: US 8,604,080 B2
(45) Date of Patent: Dec. 10, 2013

(54) HIGH DOSE GLYCINE AS A TREATMENT FOR OBSESSIVE-COMPULSIVE DISORDER AND OBSESSIVE COMPULSIVE SPECTRUM DISORDERS

(76) Inventor: W. Louis Cleveland, New York, NY (US)

(*) Notice: Subject to any disclaimer, the term of this patent is extended or adjusted under 35 U.S.C. 154(b) by 856 days.

(21) Appl. No.: 12/527,007

(22) PCT Filed: Feb. 4, 2008

(86) PCT No.: PCT/US2008/052925
§ 371 (c)(1),
(2), (4) Date: Aug. 13, 2009

(87) PCT Pub. No.: WO2008/100727
PCT Pub. Date: Aug. 21, 2008

(65) Prior Publication Data
US 2010/0113598 A1 May 6, 2010

Related U.S. Application Data

(60) Provisional application No. 60/901,176, filed on Feb. 14, 2007.

(51) Int. Cl.
*A61K 31/195* (2006.01)

(52) U.S. Cl.
USPC .......................................................... 514/561

(58) Field of Classification Search
USPC .......................................................... 514/561
See application file for complete search history.

(56) References Cited

U.S. PATENT DOCUMENTS

2004/0157926 A1* 8/2004 Heresco-Levy et al. ...... 514/561

OTHER PUBLICATIONS

Phillips, The American Journal of Psychiatry, 1991;148(9):1138-1149.*
Tanquary et al., Am J Psychiatry, 1992;149(9):1283-1284.*
Tsai et al., Biol Psychiatry, 2004;55:452-456.*
A. P. Association, Diagnostic and Statistical Manual of Mental Disorders DSM-IV-TR Fourth Edition, 4th ed. Amer Psychiatric Pub, 2000, pp. 456-463.
Berman, R. M. et al., "Antidepressant effects of ketamine in depressed patients," Biological Psychiatry, vol. 47, No. 4, pp. 351-354, Feb. 2000.
Bjornsson, A. S. et al., "Body dysmorphic disorder," Dialogues Clin Neurosci, vol. 12, No. 2, pp. 221-232,2010.
Blanpied, T. A. et al., "Trapping channel block of NMDA-activated responses by amantadine and memantine," J. Neurophysiol., vol. 77, No. 1, pp. 309-323, Jan. 1997.
Bloch, M. H. et al., "A systematic review: antipsychotic augmentation with treatment refractory obsessive-compulsive disorder," Mol. Psychiatry, vol. 11, No. 7, pp. 622-632, Jul. 2006.
Bloch, M. H. et al., "Effects of Ketamine in Treatment-Refractory Obsessive-Compulsive Disorder," Biological psychiatry, Jul. 2012.
Burns, S. and S. Lerner, "The Effects of Phencyclidine in Man," in PCP (Phencyclidine): Historical and Current Perspectives, Ann Arbor, MI 48106: NPP Books, 1981, pp. 449-469.

(Continued)

*Primary Examiner* — San-Ming Hui
(74) *Attorney, Agent, or Firm* — Beverly W. Lubit; Greenberg Traurig, LLP

(57) ABSTRACT

The present invention provides for a method of treating OCD or an Obsessive-Compulsive Spectrum Disorder (OCSD), such as BDD or ADHD, using a high-dose glycine treatment.

24 Claims, 2 Drawing Sheets

(56) References Cited

OTHER PUBLICATIONS

Carlsson, M. L., "On the role of cortical glutamate in obsessive-compulsive disorder and attention-deficit hyperactivity disorder, two phenomenologically antithetical conditions," Acta Psychiatr Scand, vol. 102, No. 6, pp. 401-413, Dec. 2000.

Castle, D. J. and Phillips, K. A., "Obsessive-compulsive spectrum of disorders: a defensible construct?" Aust. N. Z. J. Psychiatry, 40(2): 114-120 (2006).

Cleveland, W. L. et al., "High-dose glycine treatment of refractory obsessive-compulsive disorder and body dysmorphic disorder in a 5-year period," Neural Plasticity, 2009:768398 (2009).

Coric, V. et al., "Beneficial effects of the antiglutamatergic agent riluzole in a patient diagnosed with obsessive-compulsive disorder and major depressive disorder," Psychopharmacology (Berl.), vol. 167, No. 2, pp. 219-220, May 2003.

Coric, V. et al "Riluzole Augmentation in Treatment-Resistant Obsessive—Compulsive Disorder: An Open-Label Trial," Biological Psychiatry, vol. 58, No. 5, pp. 424-428, Sep. 2005.

Domino, E. F. et al., "Chapter 18: Abnormal mental states induced by phencyclidine as a model of schizophrenia," in "PCP (phencyclidine): Historical and Current Perspectives", edited by E. F. Domino, © 1981 NPP Books, Ann Arbor, MI.

Domino, E. F. et al., "Phencyclidine/Schizophrenia: one view toward the past, the other to the future," Schizophr. Bull., 38(5): 914-919 (2012).

Elahi, F. et al., "A case of clarithromycin psychosis," The Psychiatrist, 28: 98-99 (2004).

Feusner, J. D. et al., "Abnormalities of visual processing and frontostriatal systems in body dysmorphic disorder," Arch. Gen. Psychiatry, vol. 67, No. 2, pp. 197-205, Feb. 2010.

Fumagalli, E. et al., "Riluzole enhances the activity of glutamate transporters GLAST, GLT1 and EAAC1," European Journal of Pharmacology, vol. 578, No. 2-3, pp. 171-176, Jan. 2008.

Graybiel, A. M. and S. L. Rauch, "Toward a neurobiology of obsessive-compulsive disorder," Neuron, vol. 28, No. 2, pp. 343-347, Nov. 2000.

Greenberg, W. M. et al., "Adjunctive glycine in the treatment of obsessive-compulsive disorder in adults," Journal of Psychiatric Research, 43: 664-670 (2009).

Heresco-Levy, U. et al., "Efficacy of high-dose glycine in the treatment of enduring negative symptoms of schizophrenia," Arch. Gen. Psychiatry, 56(1): 29-36 (1999).

Hezel, D. M. et al., "Memantine as an augmenting agent for severe pediatric OCD," Am J Psychiatry, vol. 166, No. 2, p. 237, Feb. 2009.

Huang, W. T. et al., "Involvement of brain glutamate release in pyrogenic fever," Neuropharmacology, vol. 41, No. 7, pp. 811-818, Dec. 2001.

Insel, T. R. et al., "Obsessive-compulsive disorder with psychotic features: a phenomenologic analysis," Am J Psychiatry, vol. 143, No. 12, pp. 1527-1533, Dec. 1986.

Javitt, D. C. et al., "Adjunctive high-dose glycine in the treatment of schizophrenia," Int. J. Neuropsychopharmacol., 4 (4): 385-391 (2001).

Kanwisher et al. (Kanwisher, N. et al., "The fusiform face area: a module in human extrastriate cortex specialized for face perception," J. Neurosci., vol. 17, No. 11, pp. 4302-4311, Jun. 1997.

Krystal, J. H. et al., "Subanesthetic effects of the noncompetitive NMDA antagonist, ketamine, in humans. Psychotomimetic, perceptual, cognitive, and neuroendocrine responses," Arch. Gen. Psychiatry, 51(3): 199-214 (1994).

Luby, E. D. et al., "Model psychoses and schizophrenia," Am. J. Psychiatry, 119: 61-67 (1962).

Luby, E. D. et al., "Study of a new schizophrenomimetic drug; sernyl," AMA Arch. Neurol. Psychiatry, 81(3): 363-369 (1959).

Malhotra, A. K. et al., "Ketamine-induced exacerbation of psychotic symptoms and cognitive impairment in neuroleptic-free schizophrenics," Neuropsychopharmacology, 17(3): 141-150 (1997).

Malhotra, A. K. et al., "NMDA receptor function and human cognition: the effects of ketamine in healthy volunteers," Neuropsychopharmacology, 14(5): 301-307 (1996).

Manev, H. et al., "Macrolide antibiotics protect neurons in culture against the N-methyl-d-aspartate (NMDA) receptor-mediated toxicity of glutamate," Brain Research, vol. 624, No. 1-2, pp. 331-335, Oct. 1993.

Merritt's Neurology, Tenth Edition, Edited by Rowland, L. P., Lippincott Williams & Wilkins, Philadephia, PA (2000), contents pp. i-x.

Mothet, J. P. et al., "D-serine is an endogenous ligand for the glycine site of the N-methyl-D-aspartate receptor," Proc. Natl. Acad. Sci. U.S.A., vol. 97, No. 9, pp. 4926-4931, Apr. 2000.

Olney, J. W. et al., "NMDA antagonist neurotoxicity: mechanism and prevention," Science, vol. 254, No. 5037, pp. 1515-1518, Dec. 1991.

Pasquini, M et al., "Memantine augmentation for refractory obsessive—compulsive disorder," Progress in Neuro-Psychopharmacology and Biological Psychiatry, vol. 30, No. 6, pp. 1173-1175, Aug. 2006.

Phillips, K. A. "11. How to Successfully Treat Body Dysmorphic Disorder with Medication," in Understanding Body Dysmorphic Disorder, 1st ed., Oxford University Press, USA, 2009, pp. 155-187.

Phillips, K. A. "9. What Causes Body Dysmorphic Disorder? Clues to an Unsolved Puzzle," in Understanding Body Dysmorphic Disorder, 1st ed., Oxford University Press, USA, 2009, pp. 127-139.

Phillips, K. A. et al., "Advancing DSM: Dilemmas in Psychiatric Diagnosis," 1st ed. Amer Psychiatric Pub, 2002.

Phillips, K. A. et al., "16. Anorexia Nervosa, Obsessive-Compulsive Disorder, Koro, and Other Disorders—Are the Relatives of BDD?," in The Broken Mirror: Understanding and Treating Body Dysmorphic Disorder, Rev Exp., Oxford University Press, USA, 2005, pp. 311-333.

Phillips, K. A. et al., "2. What is Body Dysmorphic Disorder?:" in Understanding Body Dysmorphic Disorder, 1st ed., Oxford University Press, USA, 2009, pp. 13-24.

Phillips, K. A. et al., "Body dysmorphic disorder: some key issues for DSM-V," Depress Anxiety, vol. 27, No. 6, pp. 573-591, Jun. 2010.

Phillips, K. A. et al., "Pharmacotherapy for body dysmorphic disorder: treatment received and illness severity," Ann Clin Psychiatry, vol. 18, No. 4, pp. 251-257, Dec. 2006.

Phillips, K. A. et al., "Should an obsessive-compulsive spectrum grouping of disorders be included in DSM-V?," Depress Anxiety, vol. 27, No. 6, pp. 528-555, Jun. 2010.

Pittenger, C. et al., "Riluzole Augmentation in Treatment-Refractory Obsessive-Compulsive Disorder," Journal of Clinical Psychopharmacology, vol. 28, No. 3, pp. 363-367, Jun. 2008.

Poyurovsky, M. et al., "Memantine for treatment-resistant OCD," Am J Psychiatry, vol. 162, No. 11, pp. 2191-2192, Nov. 2005.

Rosenberg, D. R. et al., "Decrease in caudate glutamatergic concentrations in pediatric obsessive-compulsive disorder patients taking paroxetine," J Am Acad Child Adolesc Psychiatry, vol. 39, No. 9, pp. 1096-1103, Sep. 2000.

Rosenberg, D. R. et al.,"Brain anatomy and chemistry may predict treatment response in paediatric obsessive-compulsive disorder," Int. J. Neuropsychopharmacol., vol. 4, No. 2, pp. 179-190, Jun. 2001.

Scahill, L. et al., "Contemporary assessment and pharmacotherapy of Tourette syndrome," NeuroRx, vol. 3, No. 2, pp. 192-206, Apr. 2006.

Sharp, F. R. et al., "Phencyclidine induction of the hsp 70 stress gene in injured pyramidal neurons is mediated via multiple receptors and voltage gated calcium channels," Neuroscience, vol. 62, No. 4, pp. 1079-1092, Oct. 1994.

Waziri R., "Glycine therapy of schizophrenia," Biol. Psychiatry, 23(2): 210-211 (1988).

* cited by examiner

HIGH DOSE GLYCINE AS A TREATMENT FOR OBSESSIVE-COMPULSIVE DISORDER AND OBSESSIVE COMPULSIVE SPECTRUM DISORDERS

This application is a U.S. national stage application of and claims priority to PCT/US2008/052925, filed Feb. 4, 2008, which claims priority to U.S. Provisional application 60/901,176, filed Feb. 14, 2007, both of which are incorporated by reference in their entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Obsessive-Compulsive Disorder (OCD) is the fourth most prevalent psychiatric disorder with a worldwide lifetime prevalence rate of about 2.5% (Bebbington et al., (1998) *Br. J. Psychiatry* 173:2-6). In the U.S., OCD affects approximately 3.3 million Americans (National Institutes of Mental Health). For example, in 1990, OCD cost the United States about 8.4 billion in social and economic losses, which accounts for ~6% of the total mental health costs. OCD typically begins in early childhood or adolescence and can severely affect quality of life. It affects men and women equally. However, onset of OCD is usually earlier in males (between the ages of 6 and 15) than in females (between the ages of 20 and 29). OCD has also been documented in cats and dogs (Overall et al., (2002) *J Am Vet Med Assoc.* 221(10):1445-52).

In addition to therapeutics, such as serotonin reuptake inhibitors (SRI) or selective serotonin reuptake inhibitors (SSRI), current available treatments for OCD include cognitive psychotherapy (CT) and/or behavioral psychotherapy (BT), either alone or in combination with OCD therapeutics. Acceptance and compliance with CT and/or BT is often difficult and specific methods may need to be matched with specific compulsions or obsessions. Treatment with SRIs and SSRIs alone also may be ineffective in diminishing OCD symptoms. Such a protocol must be closely monitored in subjects, particularly adolescents, for treatment can be associated with negative side effects, such as dizziness, nervousness, insomnia, alterations in blood pressure, sedation, weight gain, irregular heart beats, and nausea. According to Hollander and Wong (*Primary Psychiatry*, 1995, 2(2): 28-33), 50-60% of OCD patients respond to an initial trial of an SSRI, but this claim is made on the basis of very short trials. According to D. J. Stein, a leading OCD researcher, "there is a paucity of longer-term trials, data on symptom remission and functional improvement, and data on treatment effectiveness in wider clinical practice." (Stein, J. C. et al., (2007) *CNS Spectr.* 12(2 Suppl 3): 28-35). Thus, there is a need to develop improved and effective methods for treating obsessive-compulsive disorder.

SUMMARY OF THE INVENTION

The invention is based, in part, on the finding that glycine treatment is an effective treatment for OCD in that a high dose treatment ameliorates the obsessive and compulsive behaviors associated with the psychiatric disorder.

One aspect of the present invention provides for a method of treating OCD (with or without co-morbidities) or an OCSD in a subject by administering to the subject an effective amount of a compound or a pharmaceutically acceptable salt thereof. In one embodiment, the compound can be an NMDA receptor agonist. In another embodiment, the subject can be further administered a glycine transporter inhibitor. In yet another embodiment, the subject can be further administered an effective amount of arginine. The effective amount of arginine can be at least about 0.01, 0.015, 0.02, 0.025, 0.03, 0.035, 0.04, 0.045, or 0.05 g/kg body weight/day. In various embodiments, the compound comprises at least Formula I:

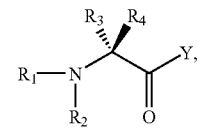

wherein $R_1$ or $R_2$ is —H, —$C_1$-$C_6$ alkyl, —$C_2$-$C_6$ alkenyl, —$C_2$-$C_6$ alkynyl, -aryl, —($C_1$-$C_6$ alkyl)-aryl, —$OR_5$, —CN, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$; $R_3$ or $R_4$ is —H, —$C_1$-$C_6$ alkyl, —$C_2$-$C_6$ alkenyl, —$C_2$-$C_6$ alkynyl, -aryl, —($C_1$-$C_6$ alkyl)-aryl, -5 or 6-membered aromatic or non-aromatic heterocycle or —($C_1$-$C_6$ alkyl)-(5 or 6-membered aromatic or non-aromatic heterocycle), wherein the —$C_1$-$C_6$ alkyl, —$C_2$-$C_6$ alkenyl, —$C_2$-$C_6$ alkynyl, -aryl, —($C_1$-$C_6$ alkyl)-aryl, -5 or 6-membered aromatic or non-aromatic heterocycle or —($C_1$-$C_6$ alkyl)-(5 or 6-membered aromatic or non-aromatic heterocycle) group is unsubstituted or optimally substituted with one or more of the following groups: -halo, —$OR_5$, —CN, —$C_1$-$C_6$ alkyl, —$C_2$-$C_6$ alkenyl, —$C_2$-$C_6$ alkynyl, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$; and Y is -halo, —$OR_5$, —CN, —$C_1$-$C_6$ alkyl, —$C_2$-$C_6$ alkenyl, —$C_2$-$C_6$ alkynyl, -aryl, —($C_1$-$C_6$ alkyl)-aryl, —$CF_3$, —$OCF_3$, —$NO_2$, —$NH_2$, —NH($C_1$-$C_6$ alkyl), —N($C_1$-$C_6$ alkyl)$_2$, —NHNH—$R_5$, where $R_5$=$R_1$ or $R_3$. In some embodiments, the compound can be glycine

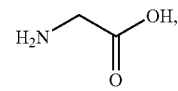

D-serine

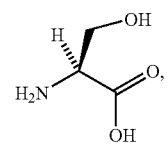

D-alanine

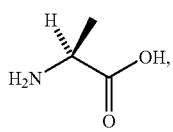

D-cycloserine

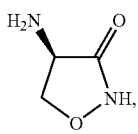

or a derivative thereof. In a particularly useful antibody, the compound is glycine. Glycine can be administered at a concentration of at least about 0.05, 0.1, 0.2, 0.3, 0.4, 0.5, 0.6, 0.7, 0.8, 0.9, 1.0, 1.1, 1.2, or 1.5 g/kg body weight/day. In other embodiments, the compound can be a glycine pro-drug such as milacemide, while in some embodiments the compound can be a glycinamide,

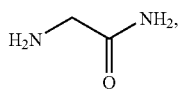

a glycine ester

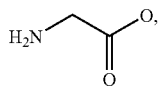

or a derivative thereof. In further embodiments of the invention, the glycine derivative can be N-benzyloxycarbonyl-glycine (Z-Glycine) or 1-Aminocyclopropanecarboxylic acid (ACPC) and the glycinamide derivative can be N-acetyl,N'-benzylglycinsmide or Z-glycinamide. In some embodiments, the method can further comprise administering an effective amount of a therapeutic composition to the subject, where the therapeutic composition is different than the NMDA receptor agonist. The therapeutic composition can be a Selective Serotonin Reuptake Inhibitor (SSRI), a neuroleptic, an anti-convulsant, an anti-depressant, an antiandrogen, or a combination of the therapuetics. In one embodiment, administering can occurs via subcutaneous, intra-muscular, intra-peritoneal, or intravenous injection; infusion; oral, nasal, or topical delivery, or a combination of the various routes. In some embodiments, the administration of the compound, arginine, and therapeutic composition occurs sequentially in any order. In other embodiments, the administration of the compound, arginine, and therapeutic composition occurs simultaneously. In another embodiment of the invention, the SSRI can be citalopram, escitalopram oxalate, fluoxetine, fluvoxamine maleate, paroxetine, sertraline, or dapoxetine. In some embodiments, the neuroleptic is a Typical Antipsychotic or an Atypical antipsychotic. The neuroleptic can be phenothiazine, butyrophenone, clozapine, olanzapine, risperidone, quetiapine, ziprasidone, melperone, or paliperidone. In further embodiments, the anti-depressant comprises a monoamine oxidase inhibitor, a Reversible Inhibitor of monoamine oxidase A (RIMA), a Dopamine reuptake inhibitor (DART), a Norepinephrine-dopamine reuptake inhibitor, a Norepinephrine reuptake inhibitor (NRI), a Serotonin-norepinephrine reuptake inhibitor (SNRT), a Selective serotonin reuptake enhancer (SSRE), a Tricyclic antidepressant (TCA), a Tetracyclic antidepressant, an NK1 receptor antagonists, or an Noradrenergic and specific serotonergic antidepressant (NaSSA). In other embodiments, the anti-convulsant comprises Aldehydes, Aromatic allylic alcohols, Barbiturates, Benzodiazepines, Bromides, Carbamates, Carboxamides, Fatty acids, Fructose derivatives, GABA analogs, Hydantoins, Oxazolidinediones, Propionates, Pyrimidinediones, Pyrrolidines, Succinimides, Sulfonamides, Triazines, Ureas, or Valproylamides. In yet some embodiments, the antiandrogen can be clomiphene citrate or a nonsteroidal androgen receptor antagonist. In another embodiment of the invention, the method can further comprise measuring bioavailability of glycine in the subject's brain, wherein bioavailability is measured using proton magnetic resonance spectroscopy. In one embodiment, the subject is a mammal. In particularly useful embodiments, the subject can be a human, dog, or a cat. In various embodiments of the invention, the obsessive-compulsive spectrum disorder (OCSD) comprises body dysmorphic disorder (BDD), compulsive skin picking, Tourette syndrome, Attention Deficit/Hyperactivity Disorder, anorexia nervosa, antisocial personality disorder (ASPD), autism, basal ganglia disorder, borderline personality disorder (BPD), bulimia, depersonalization disorder, epilepsy, Huntington's disease, hypochondriasis, kelptomania, personality disorder, pathologic gambling, sexual compulsions, Sydenham's chorea, torticollis, trichotillomania, or Pediatric Autoimmune Neuropsychiatric Disorders Associated with Streptococcal infections.

Another aspect of the invention provides for a method for determining bioavailability of glycine in the brain of a subject having obsessive-compulsive disorder (OCD) or an obsessive-compulsive spectrum disorder (OCSD), wherein the subject has been administered at least about 0.1 g/kg body weight/day of glycine. The method entails measuring endogenous brain glycine in a subject using proton magnetic resonance spectroscopy. In one embodiment, glycine can be administered by infusion or oral delivery. In other embodiments, the method can further comprising administering an effective amount of arginine to the subject. The effective amount of arginine can be at least about 0.01, 0.015, 0.02, 0.025, 0.03, 0.035, 0.04, 0.045, or 0.05 g/kg body weight/day. In some embodiments, the method can further entail administering an effective amount of a therapeutic composition to the subject, the therapeutic composition being different than glycine. In further embodiments, the therapeutic composition is a Selective Serotonin Reuptake Inhibitor (SSRI), a neuroleptic, an anti-convulsant, an anti-depressant, an antiandrogen, or a combination of such therapeutics. In various embodiments of the invention, the administering can occur via subcutaneous, intra-muscular, intra-peritoneal, or intravenous injection; infusion; oral, nasal, or topical delivery. In some embodiments, the administration of glycine, arginine, and the therapeutic composition can occur sequentially in any order, while in other embodiments administration of glycine, arginine, and the therapeutic composition can occur simultaneously. In one embodiment, the SSRI can be citalopram, escitalopram oxalate, fluoxetine, fluvoxamine maleate, paroxetine, sertraline, or dapoxetine. In another embodiment, the neuroleptic can be a Typical Antipsychotic or an Atypical antipsychotic. In a further embodiment, the neuroleptic can be phenothiazine, butyrophenone, clozapine, olanzapine, risperidone, quetiapine, ziprasidone, melperone, or paliperidone. In other embodiments, the anticonvulsants can be Aldehydes, Aromatic allylic alcohols, Barbiturates, Benzodiazepines, Bromides, Carbamates, Carboxamides, Fatty acids, Fructose derivatives, GABA analogs, Hydantoins, Oxazolidinediones, Propionates, Pyrimidinediones, Pyrrolidines, Succinimides, Sulfonamides, Triazines, Ureas, or Valproylamides. In other embodiments, the anti-depressant can be a monoamine oxidase inhibitor, a Reversible Inhibitor of monoamine oxidase A (RIMA), a Dopamine reuptake inhibitor (DART), a Norepinephrine-dopamine reuptake inhibitor, a Norepinephrine reuptake inhibitor (NRI), a Serotonin-norepinephrine reuptake inhibitor (SNRT), a Selective serotonin reuptake enhancer (SSRE), a Tricyclic antidepressant (TCA), a Tetracyclic antidepressant, an NK1 receptor antagonists, or an Noradrenergic and specific serotonergic antidepressant (NaSSA). In various embodiments, the antiandrogen can be clomiphene citrate or a nonsteroidal androgen receptor antagonist. In some embodiments of the invention, the subject is a mammal In particularly useful embodiments, the subject can be a human, dog, or a cat. In other embodiments, an obsessive-compulsive spectrum disorder (OCSD) can be body dysmorphic disorder (BDD), compulsive skin picking, Tourette syndrome, Attention Deficit/Hyperactivity Disorder, anorexia nervosa, antisocial personality disorder (ASPD), autism, basal ganglia disorder, borderline personality disorder (BPD), bulimia, depersonalization disorder, epilepsy, Huntington's disease, hypochondriasis, kelptomania, personality disorder, pathologic gambling, sexual compulsions, Sydenham's chorea, torticollis, trichotillomania, or Pediatric Autoimmune Neuropsychiatric Disorders Associated with Streptococcal infections.

A further aspect of the invention provides for a composition that encompasses an admixture of at least greater than 5, 7.5, 10, 15, 20, 25, 30, 35, 40, 45, 50, 60, 70, 80, 90, 95, 100, 110, 110, 120, or 125 g glycine and an edible matrix. In one embodiment, the edible matrix can be a crisp matrix, a candy matrix, or a combination of the matrixes. In other embodiments, the composition can be in the form of an edible bar, a cookie, tablet, wafer, or cereal. In some embodiments, the composition can further encompass a flavoring. The flavoring can be a raspberry flavoring, chocolate flavoring, vanilla flavoring, strawberry flavoring, apple flavoring, citrus flavoring, watermelon flavoring, mango flavoring, kiwi flavoring, banana flavoring, coconut flavoring, caramel flavoring, grape flavoring, blueberry flavoring, peanut flavoring, almond flavoring, tart cherry flavoring, coffee flavoring, cinnamon flavoring, ginger flavoring, mint flavoring, nutmeg flavoring, clove flavoring, ginger flavoring, peach flavoring, pear flavoring, other herbs, or a combination of any of the flavorings. In other embodiments, the composition can further encompass an artificial sweetener or a sugar. In one embodiment, the artificial sweetener can be aspartame, saccharine, sucralose, L-glucose, neotame, calcium saccharine, or a combination of the sweetener. In another embodiment, the sugar can be dextrose, maple sugar, cane sugar, beet sugar, fructose, sucrose, or a combination of such sugars. In some embodiments, the crisp matrix can be fiber, flour, soy, peanut, or a combination thereof. In other embodiments, the fiber can be a grain or a flax seed. In further embodiments, the grain comprises corn, rice, wheat, barley, oat, quinoa, or a combination thereof. In yet other embodiments of the invention, the candy matrix can be chocolate, fudge, caramel, nougat, fondant, gum, marshmallow, praline, toffee, or combination of such candy matrixes.

Another aspect of the invention further provides a method for treating a subject having obsessive-compulsive disorder (OCD) or an obsessive-compulsive spectrum disorder (OCSD), wherein the method entails administering to the subject an effective amount of a compound or a pharmaceutically acceptable salt thereof, wherein the compound comprises a glycine transporter inhibitor. In one embodiment, the method can further entail administering an effective amount of arginine to a subject. The effective amount of arginine can be at least about 0.01, 0.015, 0.02, 0.025, 0.03, 0.035, 0.04, 0.045, or 0.05 g/kg body weight/day. In some embodiments, the glycine transporter inhibitor can be sarcosine, glycyldodecylamide, N[3-(4'-fluorophenyl)-3-(4'-phenylphenoxy) propyl]sarcosine (NFPS), Organon-24461, Organon-24598, R-NPTS, or SSR504734. In other embodiments, the method can further comprise administering an effective amount of a therapeutic composition to the subject, where the therapeutic composition is different than the glycine transporter inhibitor. The therapeutic composition can be a Selective Serotonin Reuptake Inhibitor (SSRI), a neuroleptic, an anti-convulsant, an anti-depressant, an antiandrogen, or a combination of the therapuetics. In one embodiment, administering can occurs via subcutaneous, intra-muscular, intra-peritoneal, or intra-venous injection; infusion; oral, nasal, or topical delivery, or a combination of the various routes. In some embodiments, the administration of the compound, arginine, and therapeutic composition occurs sequentially in any order. In other embodiments, the administration of the compound, arginine, and therapeutic composition occurs simultaneously. In another embodiment of the invention, the SSRI can be citalopram, escitalopram oxalate, fluoxetine, fluvoxamine maleate, paroxetine, sertraline, or dapoxetine. In some embodiments, the neuroleptic is a Typical Antipsychotic or an Atypical antipsychotic. The neuroleptic can be phenothiazine, butyrophenone, clozapine, olanzapine, risperidone, quetiapine, ziprasidone, melperone, or paliperidone. In further embodiments, the anti-depressant comprises a monoamine oxidase inhibitor, a Reversible Inhibitor of monoamine oxidase A (RIMA), a Dopamine reuptake inhibitor (DART), a Norepinephrine-dopamine reuptake inhibitor, a Norepinephrine reuptake inhibitor (NRI), a Serotonin-norepinephrine reuptake inhibitor (SNRI), a Selective serotonin reuptake enhancer (SSRE), a Tricyclic antidepressant (TCA), a Tetracyclic antidepressant, an NK1 receptor antagonists, or an Noradrenergic and specific serotonergic antidepressant (NaSSA). In other embodiments, the anti-convulsant comprises Aldehydes, Aromatic allylic alcohols, Barbiturates, Benzodiazepines, Bromides, Carbamates, Carboxamides, Fatty acids, Fructose derivatives, GABA analogs, Hydantoins, Oxazolidinediones, Propionates, Pyrimidinediones, Pyrrolidines, Succinimides, Sulfonamides, Triazines, Ureas, or Valproylamides. In yet some embodiments, the antiandrogen can be clomiphene citrate or a nonsteroidal androgen receptor antagonist. In another embodiment of the invention, the method can further comprise measuring bioavailability of glycine in the subject's brain, wherein bioavailability is measured using proton magnetic resonance spectroscopy. In one embodiment, the subject is a mammal In particularly useful embodiments, the subject can be a human, dog, or a cat. In various embodiments of the invention, the obsessive-compulsive spectrum disorder (OCSD) comprises body dysmorphic disorder (BDD), compulsive skin picking, Tourette syndrome, Attention Deficit/Hyperactivity Disorder, anorexia nervosa, antisocial personality disorder (ASPD), autism, basal ganglia disorder, borderline personality disorder (BPD), bulimia, depersonalization disorder, epilepsy, Huntington's disease, hypochondriasis, kelptomania, personality disorder, pathologic gambling, sexual compulsions, Sydenham's chorea, torticollis, trichotillomania, or Pediatric Autoimmune Neuropsychiatric Disorders Associated with Streptococcal infections.

Another aspect of the invention provides for a method for treating a subject having body dysmorphic disorder (BDD) or Attention Deficit/Hyperactivity Disorder (ADHD). The method can entail administering to the subject an effective amount of a compound or a pharmaceutically acceptable salt thereof, wherein the compound comprises an NMDA receptor agonist. In one embodiment, the compound can be an NMDA receptor agonist. In another embodiment, the subject can be further administered a glycine transporter inhibitor. In yet another embodiment, the subject can be further administered an effective amount of arginine. The effective amount of arginine can be at least about 0.01, 0.015, 0.02, 0.025, 0.03, 0.035, 0.04, 0.045, or 0.05 g/kg body weight/day. In various embodiments, the compound comprises at least Formula I:

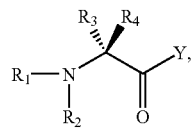

wherein $R_1$ or $R_2$ is —H, —$C_1$-$C_6$ alkyl, —$C_2$-$C_6$ alkenyl, —$C_2$-$C_6$ alkynyl, -aryl, —($C_1$-$C_6$ alkyl)-aryl, —$OR_5$, —CN, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$; $R_3$ or $R_4$ is —H, —$C_1$-$C_6$ alkyl, —$C_2$-$C_6$ alkenyl, —$C_2$-$C_6$ alkynyl, -aryl, —($C_1$-$C_6$ alkyl)-aryl, -5 or 6-membered aromatic or non-aromatic heterocycle or —($C_1$-$C_6$ alkyl)-(5 or 6-membered aromatic or non-aromatic heterocycle), wherein the —$C_1$-$C_6$ alkyl, —$C_2$-$C_6$ alkenyl, —$C_2$-$C_6$ alkynyl, -aryl, —($C_1$-$C_6$ alkyl)-aryl, -5 or 6-membered aromatic or non-aromatic heterocycle or —($C_1$-$C_6$ alkyl)-(5 or 6-membered aromatic or non-aromatic heterocycle) group is unsubstituted or optimally substituted with one or more of the following groups: -halo, —$OR_5$, —CN, —$C_1$-$C_6$ alkyl, —$C_2$-$C_6$ alkenyl, —$C_2$-$C_6$ alkynyl, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$; and Y is -halo, —$OR_5$, —CN, —$C_1$-$C_6$ alkyl, —$C_2$-$C_6$ alkenyl, —$C_2$-$C_6$ alkynyl, -aryl, —($C_1$-$C_6$ alkyl)-aryl, —$CF_3$, —$OCF_3$, —$NO_2$, —$NH_2$, —NH($C_1$-$C_6$ alkyl), —N($C_1$-$C_6$ alkyl)$_2$, —NHNH—$R_5$, where $R_5$=$R_1$ or $R_3$. In some embodiments, the compound can be glycine

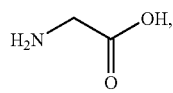

D-serine

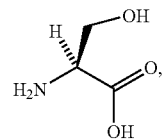

D-alanine

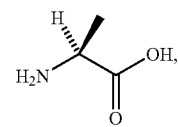

D-cycloserine

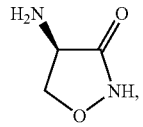

or a derivative thereof. In a particularly useful antibody, the compound is glycine. Glycine can be administered at a concentration of at least about 0.05, 0.1, 0.2, 0.3, 0.4, 0.5, 0.6, 0.7, 0.8, 0.9, 1.0, 1.1, 1.2, or 1.5 g/kg body weight/day. In other embodiments, the compound can be a glycine pro-drug such as milacemide, while in some embodiments the compound can be a glycinamide,

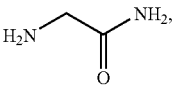

a glycine ester

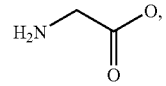

or a derivative thereof. In further embodiments of the invention, the glycine derivative can be N-benzyloxycarbonyl-glycine (Z-Glycine) or 1-Aminocyclopropanecarboxylic acid (ACPC) and the glycinamide derivative can be N-acetyl,N'-benzylglycinsmide or Z-glycinamide. In some embodiments, the method can further comprise administering an effective amount of a therapeutic composition to the subject, where the therapeutic composition is different than the NMDA receptor agonist. The therapeutic composition can be a Selective Serotonin Reuptake Inhibitor (SSRI), a neuroleptic, an anti-convulsant, an anti-depressant, an antiandrogen, or a combination of the therapuetics. In one embodiment, administering can occurs via subcutaneous, intra-muscular, intra-peritoneal, or intravenous injection; infusion; oral, nasal, or topical delivery, or a combination of the various routes. In some embodiments, the administration of the compound, arginine, and therapeutic composition occurs sequentially in any order. In other embodiments, the administration of the compound, arginine, and therapeutic composition occurs simultaneously. In another embodiment of the invention, the SSRI can be citalopram, escitalopram oxalate, fluoxetine, fluvoxamine maleate, paroxetine, sertraline, or dapoxetine. In some embodiments, the neuroleptic is a Typical Antipsychotic or an Atypical antipsychotic. The neuroleptic can be phenothiazine, butyrophenone, clozapine, olanzapine, risperidone, quetiapine, ziprasidone, melperone, or paliperidone. In further embodiments, the anti-depressant comprises a monoamine oxidase inhibitor, a Reversible Inhibitor of monoamine oxidase A (RIMA), a Dopamine reuptake inhibitor (DART), a Norepinephrine-dopamine reuptake inhibitor, a Norepinephrine reuptake inhibitor (NRI), a Serotonin-norepinephrine reuptake inhibitor (SNRT), a Selective serotonin reuptake enhancer (SSRE), a Tricyclic antidepressant (TCA), a Tetracyclic antidepressant, an NK1 receptor antagonists, or an Noradrenergic and specific serotonergic antidepressant (NaSSA). In other embodiments, the anti-convulsant comprises Aldehydes, Aromatic allylic alcohols, Barbiturates, Benzodiazepines, Bromides, Carbamates, Carboxamides, Fatty acids, Fructose derivatives, GABA analogs, Hydantoins, Oxazolidinediones, Propionates, Pyrimidinediones, Pyrrolidines, Succinimides, Sulfonamides, Triazines, Ureas, or Valproylamides. In yet some embodiments, the antiandrogen can be clomiphene citrate or a nonsteroidal androgen receptor antagonist. In another embodiment of the invention, the method can further comprise measuring bioavailability of glycine in the subject's brain, wherein bioavailability is measured using proton magnetic resonance spectroscopy. In one embodiment, the subject is a mammal In particularly useful embodiments, the subject can be a human, dog, or a cat.

DETAILED DESCRIPTION OF THE INVENTION

Figure 1:
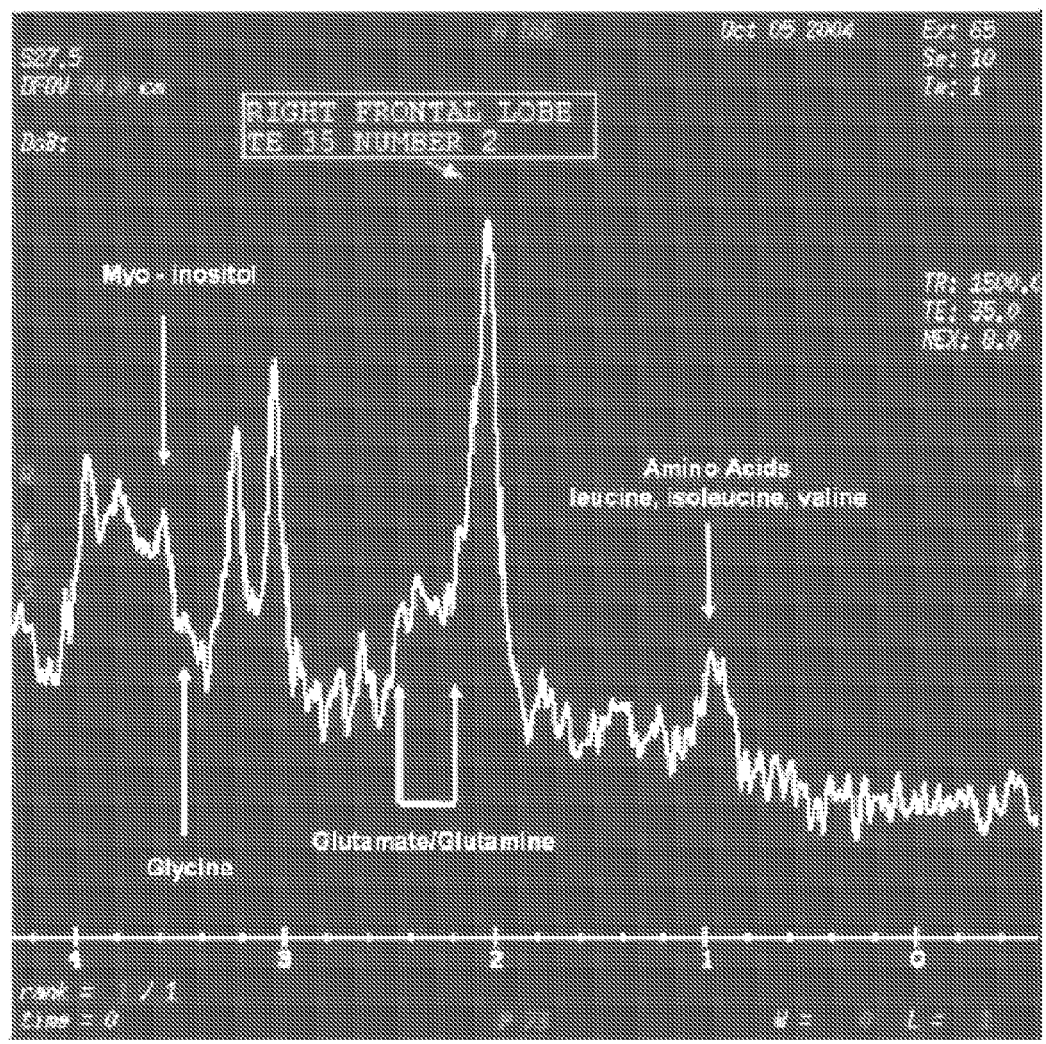
FIG. 1 depicts the magnetic resonance spectrum associated with the voxel of FIG. 2 Data obtained is from the right frontal lobe of Subject 1 patient.

The invention is based, in part, on the finding that glycine treatment is an effective treatment for OCD in that a high dose glycine treatment ameliorates the obsessive and compulsive behaviors associated with the psychiatric disorder. The present invention provides methods for treating said subjects, in addition to those subjects having an OCD-related disorder, such as an Obsessive-Compulsive Spectrum Disorder (OCSD).

DEFINITIONS

The term "pharmaceutically acceptable salt" as used herein refers to a salt of an acid and a basic nitrogen atom of a compound of the invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the invention.

Obsessive-Compulsive Disorder and Obsessive-Compulsive Spectrum Disorders

OCD is characterized by either obsessions or compulsions, or both. Obsessions are recurrent and persistent thoughts, impulses or images that are experienced as intrusive and cause marked anxiety and distress. Compulsions are repetitive behaviors (e.g. hand washing, cleaning, checking, requesting reassurance, hoarding, repeating, ordering, and the like) or mental acts (e.g. counter-images, counting, rumination, repeating prayers or words, and the like) that the person feels driven to do in response to an obsession. They can be time-consuming and interfere with the daily routine. OCD is a disorder that can, in some cases, cause a severe impairment that prevents education, employment, social activities and marriage. Subject 1, who is described in the EXAMPLES section, is such an example.

A wide range of psychiatric and medical disorders are purportedly related to OCD and form a family of disorders known as obsessive compulsive spectrum disorder (OCSD). These conditions may share common features with OCD and are grouped based on their phenomenological similarities with OCD (i.e., obsessive thinking and/or compulsive behaviors), as well as their having courses of illness, co-morbidity and family history patterns, biological abnormalities, and treatment responses similar to OCD (Castle and Phillips, (2006) *Aust N Z J Psychiatry* 40(2):114-20; Hollander and Wong, (1995) *Primary Psychiatry* 2(2): 28-32; McElroy et al., (1994) *J Clin Psychiatry* 55(Supp):33-53, which are all hereby incorporated by reference). As such, people with OCD may be diagnosed with other OCSD conditions, such as body dysmorphic disorder (BDD), compulsive skin picking, Tourette syndrome, Attention Deficit/Hyperactivity Disorder, torticollis, and trichotillomania.

Body dysmorphic disorder is a disabling disorder characterized by preoccupation with a nonexistent or slight defect in appearance (often in the face) that causes clinically significant distress and impairment. In these individuals, insight is frequently poor. Approximately half of patients are delusional and BDD is seen in 12% of OCD patients. Compulsive skin picking (CSP; also known as dermatillomania) is characterized by the repeated urge to pick at one's own skin, often to the extent that damage is caused. Damage from CSP is common on the scalp, face, extremities, and back, and is usually caused by a mixture of biting, picking, tweezing, and scratching. CSP individuals find skin picking to be gratuitious and stress relieving rather than painful. Tourette syndrome (TS) is an inherited neurological disorder that manifests during childhood. It is characterized by the presence of multiple physical tics (referred to as motor tics) and at least one vocal tic (phonic tics). Trichotillomania (TTM) is an impulse control disorder that is characterized by the repeated urge to pull out beard hair, scalp hair, eyelashes, eyebrows, nose hair, pubic hair, or other body hair.

In addition to disorders that comprise the OCD Spectrum, additional co-morbidities of OCD can further comprise depression and bipolar disorder (Castle and Phillips, (2006) *Aust N Z J Psychiatry* 40(2):114-20; Hollander and Wong, (1995) *Primary Psychiatry* 2(2): 28-32). Additionally, a connection may exist between Asperger syndrome, Huntington's disease (Cowand et al., (2006) *Curr Top Dev Biol.* 75:25-71), autism and OCD.

Attention Deficit/Hyperactivity Disorder (ADHD) is not uncommon as a co-morbidity of obsessive-compulsive disorder. ADHD is a neurological disorder that initially appears during childhood. It manifests itself with symptoms such as hyperactivity, forgetfulness, poor impulse control, and distractability. ADHD is currently considered to be a persistent and chronic syndrome with no known medical cure, and is believed to affect between 3-5% of the United States population, including both children and adults.

Some OCD cases are purportedly caused in part by childhood streptococcal infections and are termed P.A.N.D.A.S. (Pediatric Autoimmune Neuropsychiatric Disorders Associated with Streptococcal infections). The streptococcal antibodies become involved in an autoimmune process. OCD symptoms are believed to worsen following streptococcal infections such as scarlet fever, "strep throat," and the like. In one embodiment, the method entails treating a subject having OCD (with or without co-morbidities) or an OCSD. Non-limiting examples of OCSDs include body dysmorphic disorder (BDD), compulsive skin picking, Tourette syndrome, Attention Deficit/Hyperactivity Disorder, anorexia nervosa, antisocial personality disorder (ASPD), autism, basal ganglia disorder, borderline personality disorder (BPD), bulimia, depersonalization disorder, epilepsy, Huntington's disease, hypochondriasis, kelptomania, personality disorder, pathologic gambling, sexual compulsions, Sydenham's chorea, torticollis, trichotillomania, and Pediatric Autoimmune Neuropsychiatric Disorders Associated with Streptococcal infections.

The current invention is directed to a method of treating obsessive-compulsive disorder (OCD) in a subject. The current invention is also directed at treating an Obsessive-Compulsive Spectrum Disorder (OCSD) in a subject. The method comprises administering to the subject an effective amount of a compound or a pharmaceutically acceptable salt in order to treat the subject to overcome OCD or the OCSD. In one embodiment, the subject can be administered an NMDAR agonist (such as glycine), a glycine transporter inhibitor (for example, an inhibitor of the type 1 glycine transporter, GlyT1), or a combination thereof.

NMDA Receptors and Signaling

The NMDA (N-methyl-D-aspartate) receptor (NMDAR) is an ionotropic receptor for glutamate. NMDA receptor activation results in the opening of an ion channel which is nonselective to cations, allowing for the flow of $Na^+$, $K^+$ ions, and small amounts of $Ca^{2+}$ (Cull-Candy et al., (2004) *Sci STKE.* 2004(255):re16). Calcium flux through NMDARs purportedly play a role in synaptic plasticity, which is the cellular mechanism involved in learning and memory (Barco et al., (2006) *J Neurochem.* 97(6):1520-33; Pittenger et al., (2003) *Philos Trans R Soc Lond B Biol Sci* 358(1432):757-63). The NMDA receptor is both voltage-gated and ligand-dependent. The NMDAR is a heterodimer formed by 2 subunits, NR1 and NR2 subunits. NR1 subunits bind the co-agonist glycine and NR2 subunits bind the neurotransmitter glutamate. NMDA receptor activation requires binding of both glutamate and the co-agonist glycine in order for the ion channel to open efficiently (Kohr G., (2006) *Cell Tissue Res.* 326(2):439-46).

Glutamate and glycine co-activation of N-methyl-D-aspartic acid (NMDA) receptors stimulates the influx of calcium ions, which leads to a complex signal transduction cascade that includes the activation of the phosphatase, calcineurin. Calcineurin in turn dephosphorylates neuronal nitric oxide (NO) synthase (nNOS) and possibly other nitric oxide synthases leading to the production of the regulator NO from arginine via nNOS (Bredt and Snyder, 1989; Garthwaite et al., 1989). NO is a highly labile gas that freely diffuses across membranes to mediate neurotoxicity and neurotransmission (Bredt and Snyder, 1992; Lowenstein and Snyder, 1992; Bruhwyler et al., 1993; Schmidt and Walter, 1994). NO can activate soluble guanylyl cyclase (GC) to increase the production of cGMP (Bredt et al., 1989; Zhuo et al., 1994), which in turn binds to and activates cGMP-dependent kinase.

The current invention is also directed to a method of treating obsessive-compulsive disorder (OCD; with or without co-morbidities)) or an Obsessive-Compulsive Spectrum Disorder (OCSD) in a subject, wherein a subject is administered an effective amount of a compound or a pharmaceutically acceptable salt (for example, an NMDAR agonist such as glycine, and/or a glycine transporter inhibitor) in order to upregulate NMDA-receptor signaling in the subject, thereby treating subject afflicted with OCD (with or without co-morbidities) or the OCSD. In one embodiment, NMDA receptor signaling increases nNOS dephosphorylation. In another embodiment, NMDA receptor signaling increases NO production. In a further embodiment, NMDA receptor signaling increases cyclic GMP production. Because glycine is purported to cross the blood-brain barrier poorly, a high plasma concentration is needed.

NMDA Receptor Agonists

The invention provides for use of NMDA receptor agonists to treat OCD (with or without co-morbidities). Non-limiting examples of such agonists are glycine, D-serine, D-alanine, D-cycloserine, and the like (Javitt D., (2006) *Curr Opin Psychiatry.* 19(2):151-7; Javitt D., (2002) *Curr Opin Investig Drugs.* 3(7):1067-72). Glycine,

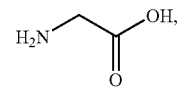

and D-serine,

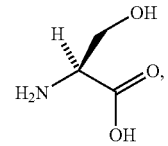

are full agonists that can cross the blood-brain barrier (BBB), and thus can be administered systemically. Since glycine is metabolized extensively at the periphery, high doses must be provided. D-serine is also an NDMA receptor co-agonist with even greater potency than glycine. D-serine is produced by serine racemase in astrocyte cells and is enriched in the same areas as NDMA receptors. D-serine can also be obtained commercially from Glytech Inc.(NY). D-alanine,

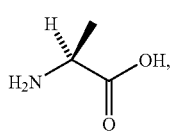

can also act as a co-agonist for the NDMA receptor (Javitt D., (2006) *Curr Opin Psychiatry.* 19(2):151-7; Javitt D., (2002) *Curr Opin Investig Drugs.* 3(7):1067-72). Two synthetic agonists exist that can modulate the NMDAR: D-cylcoserine and 1-Aminocyclopropanecarboxylic acid (ACPC). D-cylcoserine,

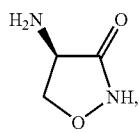

(GD Searle & Co.) is an anti-tubecrulosis agent that can cross the BBB and functions as a partial agonist. ACPC (Annovis Inc.),

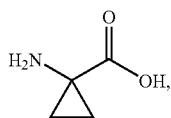

is also a partial agonist. Both partial agonists are useful in the treatment methods and can be obtained commercially. In one embodiment, the NMDAR agonist can comprise a structure of Formula I:

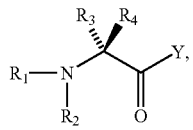

wherein $R_1$ or $R_2$ can be —H, —$C_1$-$C_6$ alkyl, —$C_2$-$C_6$ alkenyl, —$C_2$-$C_6$ alkynyl, -aryl, —($C_1$-$C_6$ alkyl)-aryl, —$OR_5$, —CN, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$;

$R_3$ or $R_4$ can be —H, —$C_1$-$C_6$ alkyl, —$C_2$-$C_6$ alkenyl, —$C_2$-$C_6$ alkynyl, -aryl, —($C_1$-$C_6$ alkyl)-aryl, -3, 5, or 6-membered aromatic or non-aromatic heterocycle or —($C_1$-$C_6$ alkyl)-(-3, 5 or 6-membered aromatic or non-aromatic heterocycle), wherein the —$C_1$-$C_6$ alkyl, —$C_2$-$C_6$ alkenyl, —$C_2$-$C_6$ alkynyl, -aryl, —($C_1$-$C_6$ alkyl)-aryl, -5 or 6-membered aromatic or non-aromatic heterocycle or —($C_1$-$C_6$ alkyl)-(3, 5, or 6-membered aromatic or non-aromatic heterocycle) group is unsubstituted or optimally substituted with one or more of the following groups: -halo, —$OR_5$, —CN, —$C_1$-$C_6$ alkyl, —$C_2$-$C_6$ alkenyl, —$C_2$-$C_6$ alkynyl, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$; and Y can be -halo, —$OR_5$, —CN, —$C_1$-$C_6$ alkyl, —$C_2$-$C_6$ alkenyl, —$C_2$-$C_6$ alkynyl, -aryl, —($C_1$-$C_6$ alkyl)-aryl, —$CF_3$, —$OCF_3$, —$NO_2$, —$NH_2$, —NH($C_1$-$C_6$ alkyl), —N($C_1$-$C_6$ alkyl)$_2$, —NHNH— $R_5$, where $R_5$=$R_1$ or $R_3$.

In one embodiment of the invention, Y of Formula I can be -halo, —$OR_5$, —$C_1$-$C_6$ alkyl, —$C_2$-$C_6$ alkenyl, —$C_2$-$C_6$ alkynyl, -aryl, —($C_1$-$C_6$ alkyl)-aryl, —$NH_2$, or —NH($C_1$-$C_6$ alkyl), where $R_5$=$R_1$ or $R_3$. In some embodiments, $R_1$ of Formula I can be —$C_2$-$C_6$ alkyl, —$C_3$-$C_6$ alkyl, or —$C_2$-$C_4$ alkyl. In another embodiment, $R_2$ of Formula I can be —H, —$CH_3$, —$C_1$-$C_6$ alkyl, —$C_2$-$C_6$ alkyl, —$C_3$-$C_6$ alkyl, —$C_2$-$C_4$ alkyl. In further embodiments, $R_3$ or $R_4$ of Formula I can be —H, —$C_1$-$C_6$ alkyl, CH2-O—$R_5$, CH2-$R_5$, where $R_5$=$R_1$ or $R_3$. In other embodiments, $R_3$ or $R_4$ of Formula I can be —H, —$C_1$-$C_6$ alkyl, CH2-O—$R_5$, CH2-$R_5$, where $R_5$=$R_1$ or $R_3$. In certain embodiments of the invention, $R_3$ or $R_4$ of Formula I can be CH2-O—$R_5$ or CH2-$R_5$, where $R_5$=—H or —OH. In a particular embodiment, $R_3$ and Y can combine to form ring. In another embodiment, $R_3$ and $R_4$ can combine to form a ring, such as a purine.

In some embodiments of the invention, the NMDAR agonist can be glycine, D-serine, D-alanine, D-cycloserine, or a derivative thereof The amino acid agonists or commercially available agonists may be derivatized, for example, bearing modifications resulting in a variation of the original product (a variant). These modifications can be covalent in nature, and include for example, chemical bonding with lipids, other organic moieties, inorganic moieties, and polymers. The R groups of an NMDA receptor agonist can also be substituted with different R groups (for example, as shown in Formula I) so long as the NMDA receptor agonist maintains its ability to bind to the glycine site on the NMDAR. In a particularly useful embodiment, the NMDAR agonist is glycine. In other embodiments, glycine can be administered at a concentration of at least about 0.05, 0.1, 0.2, 0.3, 0.4, 0.5, 0.6, 0.7, 0.8, 0.9, 1.0, 1.1, 1.2, or 1.5 g/kg body weight/day. In one embodiment, glycine can be administered at a concentration of at least 0.1 g/kg body weight/day. In another embodiment, glycine can be administered at a concentration of at least about 0.8 g/kg body weight/day. In a further embodiment, the glycine derivative can be N-benzyloxycarbonyl-glycine (Z-Glycine),

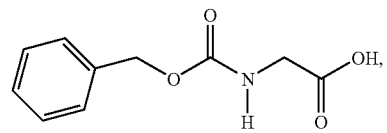

or 1-Aminocyclopropanecarboxylic acid (ACPC),

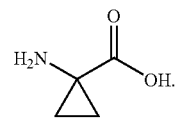

Large doses of glycine must be administered to the subject each day in order to effectively ameliorate symptoms associated with OCD or an OCSD. The invention provides compositions and formulations of the NMDAR agonists. For example, formulation of glycine "bars" with additives to sequester the taste can address the unfavorable taste since liquid formulations usually do not mask the taste (discussed below). Glycine can be obtained commercially from Medifoods (NJ).

In some individuals who have been administered a high glycine dosage, the glycine cleavage reaction generates mild hyperammonemia. Hyperammonemia is a metabolic disturbance characterised by an excess of ammonia in the blood (Albrecht et al., (2005) *Metab Brain Dis.* 20(4):253-63; Felipo et al., (2002) *Prog Neurobiol.* 67(4):259-79). In Hahn et al., (*Scan. J. Urology* (1999) 33:222-227), glycine (~18-22 grams) was infused over 30-50 minutes. That administration is similar to ingesting 20-30 g of glycine, which probably crosses into the plasma in about 2 hours or less. In healthy volunteers, Hahn et al., (*Scan. J. Urology* (1999) 33:222-227) find that 15% have no increase in plasma ammonia, 70% showed only a slight increase, and 15% showed a more marked increase, with some individuals displaying plasma ammonia concentrations of 100-120 µM, similar to what was observed in Subject 1 [See EXAMPLES]. Thus, about 15% of the population may experience mild hyperammonemia with the amount of glycine consumed according to the methods of the invention. For example, the probability of inducing hyperammonemia increases if glycine is administered in combination with valproic acid, a therapeutic that can be prescribed to epileptics and subjects afflicted with bipolar disorder. Such a situation may arise in these individuals diagnosed with epilepsy or bipolar disorder and an OCD spectrum disorder. The use of magnetic resonance spectroscopy to monitor brain ammonia would be especially useful in such instances (see discussion below and EXAMPLES).

Hyperammonemia can be controlled by administering an effective dose of L-arginine. Arginine has been used to control hyperammonemia in urea cycle disorders and other conditions (Bachman et al., (2004) *Mol Genet Metab.* 81 Suppl 1:S52-7). Thus, arginine may be used to control hyperammonemia induced by glycine consumption). A basic principle of using arginine is that it should be titrated to the minimum amount needed to control ammonia in a particular individual. Hahn et al., (*Scan. J. Urology* (1999) 33:222-227) suggest that different people have different capacities for ammonia metabolism. Consequently, the minimum amount of arginine needed for ammonia control will vary with the individual. The amount of Arginine needed (~3-4 grams per day) does not exceed much above the average amount ingested in an average diet. Thus, it is reasonable to expect it to be safe for long-term consumption. For example, in one experiment with Subject 1 (see EXAMPLES below), 3 grams of Arginine was administered with a 25-gram aliquot of glycine and the ammonia concentration, 29 µM, was the lowest recorded for Subject 1, even when no glycine was taken. For example, in another experiment, 1 gram of Arginine was used and the plasma ammonia concentration was ~94 µM, which is lower than the 118-136 µM concentration observed without arginine treatment. This suggests that 1.5-2 grams of Arginine for each 25-30 gram glycine aliquot would be adequate for Subject 1, assuming two glycine aliquots per day.

It is important to minimize arginine ingestion since it is a substrate for nitric oxide synthases (NOSs). Of the three NOS enzymes, at least one, iNOS, may be substrate limited. In individuals with inflammatory processes, increasing arginine would increase inflammation, which could be undesirable. This is suggested by an experiment with lupus mice (i.e. autoimmune), which die more quickly when fed a lot of arginine in their diet. Also, heart attack patients were recently treated with 9 grams of arginine per day and did more poorly than placebo patients. The trial was cancelled before completion.

In some embodiments of the invention, L-arginine can be administered to a subject afflicted with OCD (with or without co-morbidities) or an OCSD. In further embodiments, L-arginine can be administered sequentially to an NMDAR agonist (such as glycine, alanine, serine, cycloserine, and the like) or simultaneously with an NMDAR agonist (such as glycine, alanine, serine, cycloserine, and the like). In other embodiments, L-arginine can be administered at a concentration of at least about 0.01, 0.015, 0.02, 0.025, 0.03, 0.035, 0.04, 0.045, 0.05 g/kg body weight/day. In particularly useful embodiment, L-arginine can be administered at a concentration of at least about 0.04 g/kg body weight/day.

The current invention provides methods for determining bioavailability of glycine in the brain of a subject having OCD (with or without co-morbidities) or an OCSD. Monitoring of endogenous glycine levels in relevant brain areas is needed to monitor dose adjustment, compliance, and ammonia metabolism. Brain magnetic resonance spectroscopy (MRS) with traditional equipment does not detect a glycine peak in normal individuals (Sener, R. N., (2003) *Computerized Medical Imaging and Graphics* 27: 297-305). However, glycine peaks have been detected with brain MRS in rare individuals with an inborn error of metabolism that causes high glycine levels. Brain MRS is a valuable means for determining dosage in relevant brain areas and compliance in individuals receiving high-dose glycine therapy. In one embodiment, endogenous glycine concentration is measured in a subject that has been administered at least about 0.05, 0.1, 0.2, 0.3, 0.4, 0.5, 0.6, 0.7, 0.8, 0.9, 1.0, 1.1, 1.2, or 1.5 g/kg body weight/day of glycine. In some embodiments, endogenous glycine concentration is measured in a subject that has been administered at least about 0.1 g/kg body weight/day of glycine. In other embodiments, endogenous glycine concentration is measured in a subject that has been administered at least about 0.8 g/kg body weight/day of glycine. In some embodiments, the method of treating subjects afflicted with OCD (with or without co-morbidities) and/or OCSD can further comprise measuring glycine bioavailability. In further embodiments, bioavailability of endogenous brain glycine can be measured using proton magnetic resonance spectroscopy. For example, long echo time proton magnetic resonance spectroscopy can be used according to the invention. In other embodiments, TC-99m HMPAO (hexamethyl propyleneamine oxime) SPECT techniques can be utilized.

Other compounds can also bind to the glycine-binding site on the NMDA receptor, thus exerting an effect on NMDA activation. These NMDA receptor agonists can be glycine pro-drugs (such as milacemide,

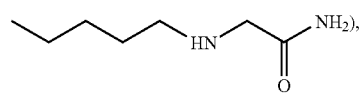

a glycinamide

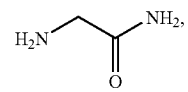

a glycine ester

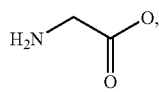

or a derivative thereof. In one embodiment, the glycinamide derivative can be N-acetyl,N'-benzylglycinsmide or Z-glycinamide.

The methods of the invention can be used to treat an animal, or a human. For example, a mammal can include, but is not limited to, a non-primate (e.g., a cow, pig, bird, sheep, goat, horse, cat, dog, rat, and mouse) and a primate (e.g., a monkey, such as a cynomolgous monkey, a chimpanzee, and a human). For example, the subject can be a non-human animal such as a bird (e.g., a quail, chicken, or turkey), a farm animal (e.g., a cow, horse, pig, or sheep), a pet (e.g., a cat, dog, or guinea pig), or laboratory animal (e.g., an animal model for a disorder). In particular, the subject according to the invention is a human.

Glycine Transporters and Inhibitors

Glycine transporters (GlyTs) mediate the uptake of glycine from the extracellular space into the cytosol. There are two types of GlyTs, GlyT1 and GlyT2, which belong to a large family of $Na^+/Cl^-$ dependent transporter transmembrane proteins (Gether et al., (2006) Trends Pharmacol Sci. 27(7):375-83; Eulenburg et al., (2005) Trends Biochem Sci. 30(6):325-33; Sonders et al., (2005) Curr Opin Neurobiol. 15(3):296-304). The transporters share approximately 50% sequence homology. GlyT1 is widely distributed throughout the CNS, present on glial cells (such as astrocytes) and neuronal cells. GlyT2 is present only in CNS regions densely populated with glycinergic neurons (Lechner S., (2006) Curr Opin Pharmacol. 6(1):75-81)

An approach to increasing glycine levels in the central nervous system (CNS) is to use glycine transport inhibitors. Glycine transport inhibitors raise synaptic glycine levels via preventing its removal from the synaptic cleft, thus augmenting NMDA function (Javitt D, (2006) Curr Opin Psychiatry. 19(2):151-7; Javitt D., (2002) Curr Opin Investig Drugs. 3(7):1067-72). A glycine transport inhibitor can target GlyT1s or GlyT2s. For example, sarcosine acts as a type 1 glycine transporter (GlyT1) inhibitor. It increases glycine concentrations in the brain thus stimulating increased NMDA receptor activation and a reduction in symptoms. Sarcosine is the N-methyl derivative of glycine,

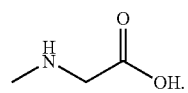

Sarcosine is found naturally as an intermediate in the metabolism of choline to glycine. In one embodiment, the glycine transporter inhibitor can be sarcosine or a derivative thereof. In other embodiments, the glycine transporter inhibitor can be glycyldodecylamide, N[3-(4'-fluorophenyl)-3-(4'-phenylphenoxy)propyl]sarcosine (NFPS), Organon-24461, Organon-24598, R-NPTS, SSR504734, or a derivative thereof. In some embodiments of the invention, the NMDAR agonist can be glycine, D-serine, D-alanine, D-cycloserine, or a derivative thereof. The glycine transporter inhibitors may also be derivatized as described above.

OCD Treatments

The invention provides methods for treating OCD and OCSD with a combination of the NMDAR agonists of the invention and/or other compounds used to treat such disorders, or other coincident disorders in a subject. Current treatments of OCD (and OCSD, such as BDD) can comprise the administering of a selective serotonin re-uptake inhibitor (SSRI), either alone or in combination with an Atypical Neuroleptic. Treatment can also comprise the administering of an SSRI, either alone or in combination with an Atypical Neuroleptic, in addition to Behavior Therapy. An anticonvulsant can also be administered in combination with the SSRI to a subject in need thereof.

SSRIs are a class of antidepressants that can be used to treat depression, anxiety disorders, and some personality disorders. For example, antidepressants can be used to treat subjects afflicted with OCD (with or without co-morbidities) or an OCSD, either alone or in combination with an NMDA receptor agonist, as described above. These drugs increase the extracellular concentration of the serotonin neurotransmitter via inhibiting its reuptake into the presynaptic cell, and subsequently increasing the level of serotonin available to bind to the postsynaptic receptor. In one embodiment, an SSRI can comprise citalopram, escitalopram oxalate, fluoxetine, fluvoxamine maleate, paroxetine, sertraline, or dapoxetine. The response to SSRIs in OCD is less robust than the response in patients diagnosed with depression. Hollander et al. report a 50-60% initial response to an SSRI administration. In some patients the apparent initial response may disappear after several months. As such, the doses need to be much higher (Hollander and Wong, (1995) Primary Psychiatry 2(2): 28-32). As the SSRI controversy has grown, statements of skepticism have become more public. SSRIs now require labeling for the putative increased suicide risk, which has led to the FDA to include warning labels. In addition, the drugs listed above can have numerous side effects, such as nausea, drowsiness, insomnia, dry mouth, and sexual dysfunction. These are concerns that are all the more imposing for OCD patients, who take these drugs at the highest doses recommended by manufacturers, and sometimes higher, as was the case for Subject 1. For example, Subject 1 took Paxil at a dose of 70 mg/day when the maximum recommended dose is 50 mg/day and was considered a non-responder. Subject 1 also was at another time prescribed Luvox at a dose of 300 mg/day, the maximum recommended dose. As a treatment for OCD, SSRIs have many deficiencies. Therefore OCD is an unsolved problem. In summary, existing pharmacotherapy is at best only partially effective. Thus, glycine treatment may address this issue in OCD and OCSD subjects.

Neuroleptics are a group of drugs that can be used to treat psychosis associated with some psychitaric disorders, such as schizophrenia, mania and delusional disorder. Neuroleptics may also be used to counter psychosis associated with a wide range of other diagnoses, such as acting as mood stabilizers, and thus being used to treat mood disorder (for example, bipolar disorder). There are currently two main classes of neuroleptics, the typical antipsychotics and atypical antipsychotics. However, a new class of neuroleptics has recently been discovered—dopamine partial agonists. In some embodiments of the invention, the neuroleptic can be a Typical Antipsychotic or an Atypical anti-psychotic. Some examples of Typical Antipsychotic include, but are not limited to phenothiazines (such as Chlorpromazine, Fluphenazine, Perphenazine, Prochlorperazine, Thioridazine, Trifluoperazine, and the like) and butyrophenone (such as Haloperidol, Droperidol, Pimozide, and the like). Non-limiting examples of Atypical anti-psychotics include clozapine, olanzapine, risperidone, quetiapine, ziprasidone, melperone, and paliperidone.

Other pharmacotherapeutics that can be used according to the method of treatment of the current invention are antiandrogens and/or anti-convulsants and/or anti-depressants other than SSRIs. Non-limiting examples of antidepressants include: Monoamine oxidase inhibitors (MAOI, such as Harmaline, Iproniazid, Isocarboxazid, Moclobemide, Nialamide, Pargyline, Phenelzine, Selegiline, Toloxatone, Tranylcypromine); Reversible Inhibitor of monoamine oxidase A (RIMA; such as Brofaromine, Moclobemide); Dopamine reuptake inhibitor (DARI; such as Amineptine, Vanoxerine); Norepinephrine-dopamine reuptake inhibitors (such as Bupropion); Norepinephrine reuptake inhibitor (NRI; such as Atomoxetine, Maprotiline, Reboxetine, Viloxazine, Wellbutrin); Serotonin-norepinephrine reuptake inhibitor (SNRI; such as Duloxetine, Milnacipran, Nefazodone Venlafaxine; Selective serotonin reuptake enhancer (SSRE; such as Tianeptine); Tricyclic antidepressants (TCA; such as Amitriptyline, Amoxapine, Butriptyline, Clomipramine, Desipramine, Dibenzepin, Dothiepin, Doxepin, Imipramine, Iprindole, Lofepramine, Melitracen, Nortriptyline, Opipramol, Protriptyline, Trimipramine); Tetracyclic antidepressants (such as Maprotiline, Mianserin, Nefazodone, Trazodone); NK1 receptor antagonists (such as Aprepitant); and Noradrenergic and specific serotonergic antidepressant (NaSSA, such as Mirtazapine).

Many anticonvulsants inhibit $Na^+$ channels, $Ca^{2+}$ channels, AMPA receptors, or NMDA receptors. Some anticonvulsants can also inhibit the metabolism of GABA or increase its release. Non-limiting examples of anticonvulsants that can be used according to the methods of this invention include: Aldehydes, Aromatic allylic alcohols, Barbiturates, Benzodiazepines, Bromides, Carbamates, Carboxamides, Fatty acids, Fructose derivatives, GABA analogs, Hydantoins, Oxazolidinediones, Propionates, Pyrimidinediones, Pyrrolidines, Succinimides, Sulfonamides, Triazines, Ureas, Valproylamides.

Antiandrogens have been shown to treat OCSDs, such as Tourette's Syndrome (Singer H., (2001) *Curr Neurol Neurosci Rep.* 1(2):195-202). Some examples include but are not limited to clomiphene citrate and nonsteroidal androgen receptor antagonists, such as flutamide, nilutamide, and bicalutamide.

OCD treatments can also entail electroshock therapy (ECT), invasive but potentially reversible deep brain stimulation, and/or irreversible lesioning with ablative psychosurgery (such as capsulotomy, cingulotomy, subcaudate tractotomy and limbic leucotomy). Some OCD patients may be helped with behavioral therapy, and often this kind of therapy is associated with the pharmacological treatment. With ECT, only a few OCD patients improve thereafter. Despite the development of the therapies described above, a significant number of OCD patients remain totally resistant to them. Additionally, some OCD subjects are discouraged because of the delay in symptom relief while drug side effects appear. These subjects tend to discontinue treatment at an early stage and a few of these patients, who are extremely ill and severely incapacitated, are candidates for neuro-surgical treatment. Surgery for mental disorders is still a controversial issue partly due to the lack of randomized and double-blind controlled studies. However, neurosurgeons claim to have been at least partially successful in treating chronic anxiety disorders by creating surgical lesions at specific locations in the neural circuitry of the brain that controls anxiety (Cosyns et al. (1994) *Adv. Tech. Stand. Neurosurg.* 21:239-279; Lippitz et al. (1997) *Acta Neuroch. Suppl.* 68:61-63). Given the risks and limited scientific evaluation, the current treatments (such as ECT, deep brain stimulation, and psychosurgery) are nonetheless inadequate for treating severe, refractory patients. Refractory OCD is defined by the failure to respond to two trials of selective serotonin reuptake inhibitors (SSRIs). The treatments pose substantial risks of serious side effects and highly questionable efficacy given the absence of blinded studies. For example, glycine treatment was highly effective in Subject 1, who represents a case of refractory OCD (see EXAMPLES below). Refractory OCD is notorious for being a "brick wall." Seedat and Stein state that "OCD patients who fail to respond to a number of trials of SSRIs may be a particularly treatment-refractory group of subjects" (*Int Clin Psychopharmacol* (1999) 14(6):353-6). The observed efficacy of glycine on treating Subject 1 is therefore quite impressive (see EXAMPLES below).

Edible Composition

Glycine is unpalatable and a large dose must be administered to the subject in order to effectively ameliorate symptoms associated with OCD (with or without co-morbidities) or an OCSD. For example, formulation of glycine "bars," "cookies," "wafers," "tablets," "cereals," and the like, with additives to sequester the taste can address the unfavorable taste since liquid formulations usually do not mask the taste. The current invention provides for a composition comprising at least about 60 g glycine and an edible matrix. In some embodiments, the composition can further comprise at least about 1, 1.5, 2, 2.5, 3, 3.5, 4, 4.5, or 5 g of L-arginine. In other embodiments, the composition is in the form of a nutrition bar, a cookie, tablet, wafer, or cereal. In further embodiments of the invention, the edible matrix can be a crisp matrix, a candy matrix, or a combination thereof.

Flavorings are added to the nutrition bar in amounts that will impart a mild, pleasant flavor. The flavoring may be present in any protein nuggets or the capsules/microcapsules or external to the nuggets and the capsules/microcapsules in the bar or other food, provided that processing is not adversely affected. The flavoring may be any of the commercial flavors typically employed in nutrition bars, such as varying types of cocoa, pure vanilla or artificial flavor, such as vanillin, ethyl vanillin, chocolate, malt, mint, yogurt powder, extracts, spices, such as cinnamon, nutmeg and ginger, mixtures thereof, and the like. It will be appreciated that many flavor variations may be obtained by combinations of the basic flavors. Suitable flavorings may also include seasoning, such as salt (sodium chloride) or potassium chloride, and imitation fruit or chocolate flavors either singly or in any suitable combination. In one embodiment, the flavoring comprises a raspberry flavoring, chocolate flavoring, vanilla flavoring, strawberry flavoring, apple flavoring, citrus flavoring, watermelon flavoring, mango flavoring, kiwi flavoring, banana flavoring, coconut flavoring, caramel flavoring, grape flavoring, blueberry flavoring, peanut flavoring, almond flavoring, tart cherry flavoring, coffee flavoring, cinnamon flavoring, ginger flavoring, mint flavoring, nutmeg flavoring, clove flavoring, ginger flavoring, peach flavoring, pear flavoring, other herbs, or a combination thereof.

Artificial sweeteners can further comprise the composition of the invention. Examples of artificial sweeteners are aspartamane, sucralose and acesulfamine-K. Most artificial sweeteners are generally hundreds of times sweeter than sugar, and provide sweetening without calories. Aspartame is approximately two hundred times sweeter than sucrose. Acesulfame-K is two hundred times sweeter than sucrose and does not break down with heat, but requires the addition of some sucrose or other sweeteners to reduce its bitter, metallic flavor that may occur. Sucralose is produced by the selective chlorination of the sucrose molecule. Sucralose is six hundred times sweeter than sugar and is free of calories. Saccharine is produced artificially by the oxidation of a sulphamic derivative of toluene. Saccharine is one of the sweetest substances known with over two hundred times the sweetening power of sugar. In one embodiment, the artificial sweetener can comprise aspartame, saccharine, sucralose, L-glucose, neotame, calcium saccharine, or a combination thereof.

Sugars also can further comprise the composition of the invention. Examples of usable sugars include dextrose, maple sugar, cane sugar, beet sugar, a fructose, a sucrose, raw sugar, brown sugar, granulated sugar, glucose, maltose, lactose and combinations of these sugars. Granulated sugar can be extracted from both sugar cane and sugar beets. In one embodiment, the sugar can comprise dextrose, maple sugar, cane sugar, beet sugar, fructose, sucrose, or a combination thereof.

Among fiber sources which may be included in the composition (such as nutrition bars or other food of the invention) are fructose oligosaccharides such as inulin, soy fiber, fruit fibre e.g. apple, guar gum, gum arabic, gum acacia, oat fiber, cellulose, whole grains and mixtures thereof The fiber can be a nutritional grain. Examples of usable grains are quinoa, millet, spelt, buckwheat, kamut, corn, rice, wheat, barley, oats, amaranth, wheat, bulgur, rye and combinations of these grains. In some embodiments, the crisp matrix can comprise fiber, flour, soy, peanut, or a combination thereof. In other embodiments, the fiber can be a grain or a flax seed. In further embodiments, the grain can comprise a corn, rice, wheat, barley, oat, quinoa, or a combination thereof Non-limiting examples of a solid crisp matrix that can further comprise the composition include soy crisps, rice crisps, corn crisps, tapioca starch in crisp form, various multi-grain crisps, and combinations thereof. In other embodiments of the invention, the edible matrix can comprise a candy matrix. Non-limiting examples of candy matrixes include chocolate, fudge, caramel, nougat, fondant, gum, marshmallow, praline, toffee, or combination thereof.

Syrups can further comprise the composition of the invention. Non-limiting examples of syrups that can be used in the composition inlcude: molasses, maple syrup, honey, corn syrup, high fructose corn syrup and inverted sugar. Molasses is a viscous liquid, containing sucrose, invert sugar, minerals and color, which is a by-product of sugar refining. Maple syrup is prepared from the sap of maple trees by boiling and evaporating to reduce the moisture content. Honey is a mixture of glucose and fructose that is collected from beehives. Corn syrup is glucose syrup that is made from the acid or enzyme hydrolysis of cornstarch. High fructose corn syrup results from enzyme hydrolysis of corn syrup to produce a product with 55-90% fructose. Invert sugar is formed from the partial or complete hydrolysis of sugar using heat, water and acid and/or invertase enzyme.

Other components that can comprise the composition of the invention are described in U.S. Pat. No. 6,900,173, and U.S. Patent Application Publication Nos. 2005/0181019 and 2006/0078593, which are hereby incorporated by reference.

Administration

If the NMDAR agonist or glycine transporter inhibitor is to be administered to a subject, it will be in the form of a pharmaceutically acceptable composition or formulation as described below, wherein the composition or formulation is free of toxicity, which satisfies FDA requirements (see *Remington: The Science and Practice of Pharmacy*, $20^{th}$ ed., Lippincott Williams & Wilkins, 2000; U.S. Pat. No. 6,030,604). Such an NMDAR agonist or glycine transporter inhibitor composition, comprising compounds or pharmaceutically acceptable salts, can be administered to a subject afflicted with OCD (with or without co-morbidities) or an OCSD. Administration can occur alone or with other therapeutically effective composition(s) (e.g., arginine, anti-convulsants, neuroleptics, SSRIs, and the like) either simultaneously or at different times.

Formulations can include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form, will generally be that amount of the compound that produces a therapeutic effect. Generally, out of one hundred percent, this amount will range from about 0.05 percent to about ninety-nine percent of active ingredient, preferably from about 5 percent to about 70 percent, most preferably from about 10 percent to about 30 percent.

Methods of preparing these formulations or compositions include the step of bringing into association a compound of the invention with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. For example, high glycine doses are poorly tolerable and thus have the possibility of generating GI side effects, such as nausea. Such unwanted side-effects can be reduced by utilizing microencapsulated, enteric coated formulations of glycine.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The NMDAR agonist or glycine transporter inhibitor composition can optionally comprise a suitable amount of a physiologically acceptable excipient. Non-limiting examples of physiologically acceptable excipients can be liquids, such as water and oils, including those of petroleum, animal, vegetable, or synthetic origin, such as peanut oil, soybean oil, mineral oil, sesame oil and the like; saline; gum acacia; gelatin; starch paste; talc; keratin; colloidal silica; urea and the like. In addition, auxiliary, stabilizing, thickening, lubricating, and coloring agents can be used. For example, the NMDAR agonist or glycine transporter inhibitor composition and physiologically acceptable excipient are sterile when administered to a subject (such as an animal; for example a human). The physiologically acceptable excipient should be stable under the conditions of manufacture and storage and should be preserved against the contaminating action of microorganisms.

Water is a useful excipient when the compound or a pharmaceutically acceptable salt of the compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The NMDAR agonist or glycine transporter inhibitor composition can be administered to the subject by any effective route, for example, orally, by infusion or bolus injection, by absorption through epithelial or mucocutaneous linings (e.g., oral, rectal, vaginal, and intestinal mucosa, etc.), intradermal, intramuscular, intraperitoneal, intravenous, subcutaneous, infusion, intranasal, epidural, oral, sublingual, intracerebral, intravaginal, transdermal, rectal, by inhalation, or topical, particularly to the ears, nose, eyes, or skin.

The NMDAR agonist or glycine transporter inhibitor composition also can be delivered in a controlled-release system or sustained-release system (see, e.g., Goodson, in *Medical Applications of Controlled Release*, vol. 2, pp. 115-138 (1984)). Other controlled or sustained-release systems previously discussed can be used as well (Langer (1990) *Science* 249:1527-1533). For example, a pump can be used (Langer (1990) *Science* 249:1527-1533; Sefton (1987) *CRC Crit. Ref Biomed. Eng.* 14:201; Buchwald et al., (1980) *Surgery* 88:507; and Saudek et al., (1989) *N. Engl. J Med.* 321:574); or polymeric materials can be used (see Langer and Wise (1985) *Medical Applications of Controlled Release*; CRC Press Inc., U.S.; Smolen and Ball (1984) *Controlled Drug Bioavailability, Drug Product Design and Performance*; Ranger and Peppas, (1983) *J. Macromol. Sci. Rev. Macromol. Chem.* 2:61; Levy et al., (1935) *Science* 228:190; During et al., (1989) *Ann. Neural.* 25:351; and Howard et al., (1989) *J. Neurosurg.* 71:105). The controlled- or sustained-release systems can be placed in proximity of a target of the compound or a pharmaceutically acceptable salt of the compound, e.g., the BBB, thus requiring only a fraction of the systemic dose. To reduce unfavorable side-effects, such as nausea, coated glycine vehicles may be used. In one embodiment, coated glycine vehicles may be used.

The subject in need can be administered a NMDAR agonist or glycine transporter inhibitor as described above. It can be administered alone or in combination with a second therapeutic, e.g., such as an SSRI, a neuroleptic, and the like, in order to treat OCD (with or without co-morbidities) or OCSDs. An SSRI and/or a neuroleptic can be co-administered with the NMDAR agonist or glycine transporter inhibitor, either sequentially, in any order, or simultaneously.

An effective amount of a NMDAR agonist or glycine transporter inhibitor refers to the amount of a therapy sufficient to reduce or ameliorate the severity and/or duration of OCD (with or without co-morbidities) or an OCSD. An effective amount of a NMDAR agonist or glycine transporter inhibitor can also be sufficient to reduce the degree and time-span of one or more symptoms associated with OCD (with or without co-morbidities) or OCSDs. Additionally, this amount can prevent the advancement of OCD (with or without co-morbidities) or an OCSD, cause regression of such a disorder, prevent the recurrence, development, onset or progression of one or more symptoms associated with OCD (with or without co-morbidities) or an OCSD. The skilled physician can determine a therapeutic dose of a NMDAR agonist or glycine transporter inhibitor that inhibits the duration of a disorder or symptoms associated with OCD (with or without co-morbidities) or an OCSD. Methods of administration of a NMDAR agonist or glycine transporter inhibitor composition have been described above.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods may be utilized to obtain similar results.

Example 1

OCD Case Study of "Subject 1" Patient

Substantial progress has been made toward a understanding of a case of obsessive-compulsive disorder (referred to as Subject 1) that has been followed for about 6 years. The model developed for this case is a "HypoNMDA" signal transduction model.

TABLE 1

Time Line of Psychiatric Illness and Treatment in Case Study

Prodrome: 24 months - age 15
Psychotherapy for "excessive anxiety" in third grade
First manifestation of frank illness: age 15
Treatment with SSRIs ± atypical neuroleptics: age 17-age 21.5
First major exacerbation of psychiatric illness apparently initiated by bilateral otitis media at age 19
Second major exacerbation of psychiatric illness apparently initiated by bilateral otitis media at age 20
Treatment with IVIG: age 21.5 - age 23
Third major exacerbation of psychiatric illness apparently initiated by medication used to remove H. pylori at age 22
No treatment from age 23-age 25.33
Glycine treatment from age 25.33 to the present time with several periods of cessation History: Interest in neuropsychiatric disorders began in 1997 with the study of an individual with obsessive-compulsive disorder (OCD) who is positive for the D8/17 B-cell marker for rheumatic fever. A longitudinal study was conducted of this individual (referred to hereafter as "Subject 1"). Factors influencing this decision were excellent access to behavioral and medical histories and blood samples.

Retrospective recollections of Subject 1 and his parents, who were unaware of the concept of OCD until a diagnosis was given at age 17, suggest that Subject 1 exhibited ritualistic behaviors as early as age 10 or 11.

Glycine Treatment of OCD/BDD.

Monitoring of Subject 1 was begun at the time that two major exacerbations, which were apparently infection-triggered, had occurred. A retrospective examination of medical records revealed that these infections (bilateral otitis media) were associated with β-hemolytic throat cultures, suggesting Group A *streptococcus* infections. 70% of β-hemolytic cultures are typically Group A. This subject therefore was a possible example of the PANDAS subtype described in Swedo et al. (*Am J Psychiatry*. (1998) 155(2):264-71; *Am J Psychiatry*. (1997) 154(1):110-2).

A lengthy trial of intravenous immune globulin was prescribed by a rheumatologist and was not found to be of benefit. Indeed, a third major exacerbation occurred in 1999 during the IVIG trial. The antibiotic regimen used by a rheumatologist in 1999 to remove *H. pylori* appeared to lead to a severe and prolonged exacerbation of OCD and BDD signs and symptoms. Streptolysin O titers were consistently negative before, during, and after the antibiotic treatment.

For this exacerbation, there was no evidence of infectious agents identified that have been associated with OCD (Group A *streptococcus*, Boma Disease Virus, Lyme *borrelia*, *Mycoplasma pneumoniae*). No evidence was found of immunological abnormalities or autoimmune activity. However, it should be emphasized that resources to search for antibodies or T-cells against brain antigens were not available. The only notable observations were signs of oral candidiasis, suggesting an antibiotic-induced superinfection. At that time, a tentative conclusion was made that the behavioral exacerbation most likely was a consequence to the antibiotic-induced superinfection. This conclusion was in part prompted by Swedo's observation that upper respiratory infections without Group A *streptococcus* could trigger exacerbations in PANDAS patients.

In June of 2002, publications on the phencyclidine model of schizophrenia were reviewed (e.g., Newcomer and Krystal, (2001) *Hippocampus* 11:529-42). As a result of better awareness of phencyclidine phenomena, an alternate interpretation of the 1999 exacerbation was considered, namely that clarithromycin was the causative agent of the exacerbation.

It is of interest that Subject 1, in 1999, proposed this interpretation. As soon as the exacerbation started, he checked the web for side effects of the three drugs (lansoprazole/amoxicillin/clarithromycin) being used to eradicate *H. pylori* and immediately discovered that psychotic symptoms had been reported as rare side effects of clarithromycin. His physician recommended that the regimen be completed since only several days remained. However, a causal role for clarithromycin was dismissed in 1999 because it was believed that it was very difficult to establish causality for putative side effects that occur only extremely rarely and because the exacerbation persisted for many months, in contrast with the clarithromycin-induced psychiatric symptoms described in the literature, which disappeared after removal of the drug.

At the time, it was believed that it was very difficult to establish causality, for putative side effects that occur extremely rarely, especially in cases where removal of the drug does not lead to an immediate reduction of putative effects. In June 2002, the reconsideration of clarithromycin as the causative agent of the 1999 exacerbation was prompted by reports in the literature that described the effects of phencyclidine on a subpopulation of patients with schizophrenia. "Administration of [phencyclidine] to stabilized chronic schizophrenia patients can trigger a recrudescence of acute psychotic symptoms lasting for up to several months" (Newcomer and Krystal, (2001) Hippocampus 11: 529-542). This phenomenon is unique to the NMDA receptor, the molecular target of phencyclidine. Representatives of other drug categories, e.g. LSD, do not cause this phenomenon (Newcomer and Krystal, (2001) *Hippocampus* 11: 529-542). The similarity of the kinetics of the response of Subject 1 to clarithromycin to the kinetics of the phencyclidine response in the subpopulation of schizophrenia patients suggested that clarithromycin was affecting neurotransmission involving the NMDA receptor.

A further search of the literature in June of 2002 revealed that Manev et al. (*Brain Res.* 624 (1-2): 331-5, 1993) had measured the ability of clarithromycin and other macrolide antibiotics to inhibit glutamate-induced cytotoxicity in cultures of human cerebellar granule neurons. The group presented evidence that clarithromycin inhibited NMDA receptor mediated excitotoxic cell death in cultured cerebellar granule neurons. Unlike NMDAR antagonists, the inhibition was downstream from the receptor. Specifically, Manev et al. (*Brain Res.* 624 (1-2): 331-5, 1993) found protection against NMDA—but not kainate-mediated excitotoxicity. The basic conclusion of the study is that clarithromycin is similar to, but weaker than, FK506, which does not act on the NMDA receptor directly but rather binds to FK506 binding protein to form a complex that inhibits the downstream activation of calcineurin, which in turn inhibits other steps such as the activation of neuronal nitric oxide synthase. The inhibitory effect of FK506 on calcineurin has been demonstrated in extensive studies by Solomon Snyder and coworkers (e.g. Dawson et al, *Proc. Natl. Acad. Sci. USA* 90: 9808-12, 1993). It should also be noted that there is now substantial literature on neurotoxic effects of calcineurin inhibitors (Cyclosporine A, FK506) in transplant patients (Bechstein, *Transpl Int* 13: 313-326, 2000). Severe symptoms, which affect as many as 5% of patients, include psychoses and hallucinations. The above analysis led the inventor to develop an hypothesis for molecular basis of Subject 1's illness. This hypothesis is referred to as the "HypoNMDA Signal Transduction Hypothesis."

HypoNMDA Signal Transduction Hypothesis. The core hypothesis consists of two basic postulates: (1) OCD symptoms in Subject 1 are due (at least in part) to a chronic, endogenous defect that leads to subnormal activity at one of the steps in one of the cellular reaction sequences induced by NMDA receptor activation, wherein the defect is assumed to be responsible for the chronic, baseline OCD symptoms seen in Subject 1; and 2) Clarithromycin either further intensifies the baseline defect or creates another defect with similar functional consequences that add to those of the baseline defect. Prior studies suggest several possibilities for the clarithromycin-induced defect. One possibility is an inhibition of calcineurin.

Potential Outcome of HypoNMDA Signal Transduction. The most important prediction of this hypothesis is that an increase in NMDA receptor activation would tend to compensate the putative hypoactivity in the critical reaction sequence and would thereby reduce symptom intensity. NMDA receptor activation above normal levels should correct the downstream signal transduction abnormality. Another important point is that a downstream defect should have different consequences from a defect at NMDA receptor. This rationalizes the failure of phencyclidine to induce OCD symptoms. The above hypothesis can be tested by administering an agonist of the NMDA receptor. Fortunately, in 2002, it was known that glycine taken at high doses is an NMDAR agonist (coagonist) that can be administered to humans. Moreover, its safety was supported by prior clinical trials.

Glycine Treatment. Glycine, an amino acid in the diet, is a co-agonist of the NMDA receptor that is thought to provide a self-limiting enhancement of NMDA receptor activation.

Glycine consumed in large amounts (~60 g/day) has been used in small trials during the past 10 years for the treatment of schizophrenia. Lower dose glycine treatments (e.g. 30 g/day) were examined in 1989 (Rosse et al., (1989) *Clin Neuropharmacol.* 12(5):416-24; Deutsch et al., (1989) *Clin Neuropharmacol.* 12(1):1-13). Studies suggest that ingestion of large amounts of glycine (i.e., 0.8 g/kg body weight/day) leads to moderately enhanced NMDA activity as a result of increased concentration of glycine at the NMDA co-agonist site (D'Souza et al., (2000) *Biol Psychiatry* 47: 450-462). In 2002, it was reasoned that if the hypoNMDA signal transduction hypothesis were correct, then high-dose glycine treatment of Subject 1 should cause reduction of his OCD, BDD, and ADHD symptoms. Subject 1 and his family were informed of these prior studies and the hypoNMDA signal transduction hypothesis and decided to initiate a glycine trial. As will be described below, this trial has led to a significant reduction in symptoms that has had a dramatic practical effect on Subject 1's life.

Implications of Calcineurin Inhibition for Obsessive Compulsive Disorder

A feature of this model that is that it links up with studies in rats, which suggest a role for calcineurin in the extinction of fear memories. In a March 2003 paper (*J Neurosci* 23(5): 1574-79), Lin et al. found that fear-training-induced phosphorylation of specific substrates is reduced after extinction trials and is accompanied by an increase in the amount and activity of calcineurin. Most importantly, they found that calcineurin inhibitors prevented in parallel both extinction-induced dephosphorylation and the actual extinction of fear memory. However, based on extensive interviews with Subject 1, excessive retention of fear memories is a major feature of OCD mentation and may be connected with the root cause of this illness. Assuming rats are similar to humans, the findings of Lin et al. raises the possibility that the chronic calcineurin-related abnormality postulated in this model is an aspect of the root cause of the abnormal handling of fear memories in OCD.

Calcineurin inhibition is also of interest in the context of findings published in the July issue of Nature Medicine (9(7): 914-920, 1993). This report described evidence for the discovery of antibodies against N-acetyl-β-D-glucosamine (GlcNAc) in sera and spinal fluid of patients with Sydenham's chorea. This finding is of great interest in relation to OCD, since OCD symptoms often accompany Sydenham's chorea, an observation that goes back at least as far as Osler (*Advances in Neurology* (1982) 35:89-92).

The most notable finding in the Cunningham et al. study (*Nature Medicine* (1993) (9(7): 914-920) is that these anti-GlcNAc antibodies bind to neuronal surfaces. Antibodies with this specificity in sera from active chorea further activate calcium/calmodulin-dependent protein kinase (CaM kinase II). In convalescent sera, enzyme-activating antibodies were not found. This result has a remarkable compatibility with this model.

Specifically, neuronal nitric oxide synthase is a known substrate of CaM kinase II (Watanabe et al., Biochem J. 372: 465-71, 2003). Phosphorylation of serine 847 attenuates activity of neuronal nitric oxide synthase. Hyperactivity of CaM kinase II by the autoimmune mechanism described by Cunningham et al. (*Nature Medicine* (1993) (9(7): 914-920) would reduce the dephosphorylation of neuronal nitric oxide synthase by calcineurin that is a consequence of NMDA activation. This is functionally equivalent to the HypoNMDA signal transduction model in which abnormal activation of calcium-dependent nitric oxide synthase is a consequence of the chronic calcineurin-related defect that was postulated for the OCD subtype represented by Subject 1. In other words an underactive phosphatase will have effects similar to an overactive kinase, at least when they compete for a common substrate, most notably in this case, nitric oxide synthase. These considerations suggest the possibility of a unified model for OCD in which autoimmune processes, which can be transient, lead to the same functional defects, and therefore the same symptoms, as other chronic factors such as genetic polymorphisms and abnormal epigenetic modifications of chromatin.

Results of Glycine Trial

Diagnosis. A diagnosis of OCD plus body dysmorphic disorder (BDD) was given by several psychiatrists, including two OCD specialists. On the basis of observed behaviors during formal testing by a psychologist at age 7, a diagnosis of attention deficit disorder was also given. No tic behaviors have ever been identified. Likewise no signs or symptoms of schizophrenia have been noted by the multiple psychiatrists who have examined this patient. Since the emergence of intense, clearly impairing signs and symptoms in 1992, the diagnosis has been stable. Although individual symptoms have varied in intensity over time, the basic spectrum of signs and symptoms appears to have been unchanged over 15 years.

Description of Main Aspects of Behavioral Impairment

As a basic principal for this case study, behavioral signs and symptoms have been regarded to be equal in importance to molecular data. Accordingly, a major effort has been made to develop a thorough and detailed history for Subject 1. A sign of major impairment is no attendance of high school beyond tenth grade.

In the 7 years before the initiation of glycine, Subject 1 was largely house bound on account of a line-crossing obsession associated with an intense fear of crime. For that period, Subject 1 also reports reluctance to leave his home on account of social discomfort due to BDD symptoms, essentially a fear of having an ugly face as a result of a large nose. The line crossing obsession is fairly complex and difficult for a lay person to understand. Subject 1 and his family were fortunate to have it clarified by a leading OCD specialist. Essentially, the obsession is triggered when Subject 1 sees a person in his neighborhood that he feels is likely to commit a violent, personal crime. This perception activates the fear and/or belief that such people are moving into his neighborhood. This is the line crossing feature of the obsession. Reports of crime in the news media also activate the obsession, provided that they occur in a "good" neighborhood. Crime events is a "bad" neighborhood are of no concern. Evidently, in the latter case there is no line crossing.

According to Subject 1's father, activation of the line crossing obsession invariably leads to a conversation that is highly repetitive due to frequent but incomplete attempts to make a particular point. An outburst of verbal anger is also a regular feature. After about 1 hour of the repetitive conversation, the psychic distress is usually dissipated. The father refers to this type of conversation as a "talkthru." These conversations were a daily feature for a number of years.

Mirror intolerance due to his BDD prevented barbershop haircuts for about 7 years before glycine treatment. Haircuts were given at home by his father.

Preservative behavior was manifest in traveling to doctors' offices and to his father's place of work. The father reports that Subject 1 insisted on taking exactly the same route on each trip and would become quite upset when traffic jams or road construction forced a change.

The exacerbation of 1999 that followed the antibiotic treatment for *H. pylori* led to a general increase in preexisting symptoms, which were mainly the line crossing obsession and BDD symptoms. There were a number of "just right" rituals but they are reported as being minor in relation to the other symptoms. Following the antibiotic treatment, Subject 1's father observed a very large increase, over a period of about two months, in a prayer ritual that was frequently performed through an entire day. Subject 1's father reports that this led to erosions on the knees that were followed by calluses. Subject 1 became very frightened by the exacerbation and did not want to be alone. This led to his father taking him on a daily basis to his place of work, which is in a secluded area of a building. Consequently, he was able to observe directly the ritualistic behavior during all waking hours. Over the course of a year, the prayer ritual gradually declined. However, both Subject 1 and his father report that ritualistic behavior in general remained elevated after the antibiotic treatment until they declined during glycine treatment.

Description of Behavioral Improvements During Glycine Treatment.

Subject 1's father reports that the first improvement was seen after about three weeks after initiation of glycine treatment, For first time in 5 years, Subject 1 left his apartment building on his own (i.e. without parent escort) and went for a short walk in front of his building. Soon after this, he began daily attendance at a nearby library on a 9 AM-5 PM weekday schedule in order to prepare for the GED exam. Leaving the house and walking to the library were done without parental assistance. The GED exam was passed on the first attempt in December 2002.

Improved personal hygiene and increased concern about appearance was reported. An interesting comment made by Subject 1 after this improvement occurred was recorded by the father: "Why did you let me sit around the house all day in dirty underwear and not take baths? Why did you let me stay up all night and sleep all day?" Subject 1's parents consider that they made (prior to glycine treatment) a sustained and major effort to normalize their son's life style and that their efforts were largely ineffective. In the above comments, it appears that Subject 1 did not consider glycine to be responsible for his changed behavior. More recently, he has expressed his belief that glycine has helped him.

Six months after starting glycine, he attended the Kaplan SAT preparation course. His scores improved by approximately 250 points, indicating an ability to work effectively and persistently toward a difficult goal.

In a progress summary compiled in September, 2003 (i.e. 1 year after initiation of glycine treatment), Subject 1's father reported a reduced intolerance of mirrors that has led to regular barbershop haircuts, without obvious stress. Subject 1's social discomfort is evidently reduced sufficiently to permit attendance at movies, restaurants, social gatherings with family friends as well as working with tutors and attendance at Kaplan SAT course. Preservative behavior during taxi rides was reported to be much reduced in the 2003 summary.

After taking the SAT test in late 2003 (see below for test scores), Subject 1 enrolled in a college with modest academic standards and maintained an A average. In the next semester (Fall 2004), he transferred to a competitive college where he continues to get excellent grades. Except for mild relapses during periods of glycine cessation, his social life has improved substantially as a result of having a circle of friends among his classmates and going on dates with girl friends. Participation in family gatherings has increased. He has traveled to another city with peers. He moves freely about his city using public transportation, even in areas that previously generated an intense fear of crime. Subject 1's parent that there are no signs of the line crossing obsession that was a major impairment before glycine treatment. BDD signs and symptoms have continued to improve during periods of sustained glycine treatment.

Cessation of Glycine Treatment Leads to a Gradual Relapse

There have been several periods of glycine cessation in which mild relapses appear to have occurred. The first cessation of glycine treatment occurred 6.5 months into the trial as a result of concerns about safety that arose in an upper respiratory infection involving a fever of 104° F. Glycine was stopped as soon as the fever began and was not restarted until 6 weeks later. In this period, the father reports an increase in the line-crossing obsession, difficulty in leaving the house and a probable increase in a hand washing ritual (in response to fear of harm, not fear of contamination). In this case, the degree of increase is less certain since the hand washing ritual was observed by parents in the evening but not during the day when they were at work. It is the father's personal estimate that in this period, there was a 20%-40% loss of the gains acquired since glycine initiation. The father reports that over a period of three months after glycine resumption, previous gains were largely recovered. The line crossing obsession and associated "talkthrus" again became reduced. At that time it was impossible to know if the deterioration was due to the infection, as has appeared to be the case in previous infections before glycine treatment, or whether it was due to glycine cessation. However, several months later, it was decided to stop glycine consumption for the same 6 week period of time when there was no infection. This led to little or no decline, suggesting that the infection caused the exacerbation as had been seen previously in the two major exacerbations that followed severe bilateral otitis media.

A 3.5 month cessation of glycine treatment in early 2004 led to a clear loss of cognitive gains that is described below. A 9 month cessation began in May 2006 as a result of a mild but unexplained weight loss. The weight loss remains unexplained, but has been reversed in recent weeks. Resumption of glycine is planned. In this lengthy cessation of glycine treatment, loss of cognitive gains has also been seen as described below. There has also been a clear increase in BDD signs and symptoms. These were much reduced before glycine cessation as indicated by an entry in Subject 1's diary that described a highly favorable experience when he saw his reflection in the window of a restaurant. Seven months after glycine cessation, clear signs of a relapse of BDD became apparent. He refused to attend two family gathering in the December holiday season on account of a fear that the strangers present might say that he looked like his mother, a fear he had in the preglycine period. At another family gathering, he asked to sit at a particular position at a dinner table so that he would not see his mother's face. This is clearly a relapse, since his father's daily diary notes occasions during sustained glycine treatment when he went to restaurants and movies with his mother and also played checkers with her. This relapse is considered mild since he still gets barbershop haircuts and socializes with peers.

An important phenomenon discovered in this case study is the slow kinetics of both improvement and relapse seen with glycine treatment. This implies that trials of glycine need to be quite lengthy if the treatment potential of glycine is to be fully measured. Finally, the dramatic improvement seen in Subject 1 during sustained glycine treatment and the relapses seen in several periods of treatment cessation strongly support the efficacy of glycine for the disorders seen in Subject 1. This efficacy is especially impressive, given that one of Subject 1's disorders is refractory OCD.

Case Study Summary. Except for twelve 0.5 mg tablets of clonazepam taken during one week in 2004, glycine was the only psychotropic reagent used by Subject 1. This case appears to be the first use of glycine alone with any psychiatric disorder. Also, no behavior therapy or psychotherapy was used during glycine treatment. Substance abuse is not an issue in this case. A stable, severe baseline was observed before glycine treatment and a stable diagnosis was noted throughout the period of illness. Robustness of improvement due to glycine treatment was successfully demonstrated by exposure to repeated academic and social stresses. Interestingly, periods of glycine cessation led to mild relapses. In addition, efficacy of glycine treatment in the Subject 1 case study was monitored for over 4.5 years. Small amounts of arginine added to the glycine treatments also was shown to bring plasma ammonia levels into the normal range.

Discussion

The glycine trial with Subject 1, which has been in progress for 4.5 years, was carried out in the absence of other psychotropic drugs (except for clonazepam used for one week). Substance abuse has never been an issue with Subject 1, who as a result of being housebound in his parents' home has been closely monitored. Finally, there was no psychotherapy or behavior therapy during this period. Thus, the results in this study are free of factors that confound many studies.

Is the Observed Improvement a Spontaneous Remission?

Although spontaneous remissions of OCD and BDD are known to occur, they are generally chronic illnesses. In this case, there was unrelenting illness for 10 years before glycine. Subject 1 and his parents report that there were no periods of even a partial remission from age 15 to age 25, when glycine treatment was initiated. They further report that during this period symptoms increased, not decreased in spite of multiple therapeutic maneuvers: 4 SSRI's and 2 atypical neuroleptics, IVIG, behavior therapy, and psychotherapy. Subject 1 and his parents consider that these maneuvers left his illness untouched. It should be noted that Subject 1's case is an example of "refractory OCD", since he failed to respond to two trials of SSRI's (Hollander et al., J Clin Psychiatry 63: 20-9, 2002). As noted by Seedat and Stein (Int. Clin Psychopharmacol. 6: 353-6, 1999), "OCD patients who fail to respond to a number of trials of SSRI's may be a particularly treatment-refractory group of patients." In view of the sustained illness before glycine treatment and the major improvement seen during glycine treatment and the relapses seen when glycine was stopped, it is unlikely that the observed improvement was a spontaneous remission.

Is the Observed Improvement a Placebo Effect?

Placebo effects can be extremely powerful. However, placebo effects tend to be transient and to collapse under the pressure of environmental stresses. A placebo effect is an unlikely cause of the improvement seen in Subject 1 because of the robust and very sustained response over a 4.5 year period that included substantial academic and social stresses.

Is the Anecdotal Data Unreliable?

Information from individuals having great emotional involvement in a case can easily be unreliable. This problem has been addressed by focusing on objective information. For example, high school attendance records, Kaplan practice test scores, GED diploma, and medical reports are written records from third parties. Medication history is supported by written records made by the father and empty medicine containers, which were retained as a record of prescribed doses. Most of the written records have been compiled by the father, who has a clear understanding of the difference between objective and subjective information. The available objective evidence is sufficient to justify the claim that a substantial improvement has occurred.

Example 2

Hyponmda Signal Transduction and Brain Imaging

The presence of glycine in brain was monitored by magnetic resonance spectroscopy. SPECT scans document brain abnormality as discussed below.

Brain Scans for Subject 1 Case Study. Other observations support a HypoNMDA signal transduction model in which abnormal activation of calcium-dependent neuronal nitric oxide synthase plays a role. Most notable are four HMPAO (hexamethyl propyleneamine oxime, TC-99m) SPECT scans done over a period of five years from 1999 to 2004. The impression of the radiologist for the first scan in 1999 was as follows: "Marked heterogeneous and decreased cortical uptake is noted throughout both cerebral hemispheres. In addition, severe white matter hypoperfusion is also noted." Additional scans show essentially identical results. A semiquantitative analysis done by the radiologist suggests that the basal ganglia, thalamus and anterior temporal regions are normal relative to the cerebellum, whereas the frontal, parietal and posterior temporal to occipital are down. These scans are high quality data since they document the reproducibility of the hypoperfusion phenomenon and since they were obtained when Subject 1 was not on prescription medication of any kind and also not on any high-dose nutritional supplements. The Four HMPAO-SPECT scans done over a period of five years reproducibly indicate abnormal blood flow in brain. An approximate 25% reduction in blood flow was observed in frontal areas relative to cerebellum. No change was noted even after glycine administration. In addition, four MRI scans, including two with MRS, were performed, one of which was carried out during glycine consumption (see discussion below and FIGS. 1-2).

These scans appear consistent with this model, which predicts chronic hypoactivity of calcium-dependent neuronal nitric oxide synthase due to insufficient calcineurin activity. For example, evidence in the literature suggests that NO generated in response to NMDA activation in vivo may mediate increases in local blood flow during increases in neuronal activity in response to excitatory amino acids (e.g. Faraci et al. Circulation Research 72: 476-80, 1993). However, the model will need extension to predict the anatomical features of these scans and to incorporate the effects of the multiple factors that control cerebral blood flow.

Magnetic Resonance Spectroscopy (MRS) for Monitoring Glycine Concentrations in Specific Areas of the Brain. Brain MRS with traditional equipment does not detect a glycine peak in normal individuals (Sener, R. N., (2003) *Computerized Medical Imaging and Graphics* 27: 297-305). Glycine peaks have been detected with brain MRS in rare individuals with an inborn error of metabolism that causes high glycine levels. This Subject 1 case study presents the first detection and measurement of a glycine peak in the brain of an individual treated with glycine. This is an important observation since it provides direct evidence in human for an increase in brain glycine concentration following high-dose glycine ingestion. Moreover, brain MRS is a valuable means for determining the correct treatment dosage to obtain a therapeutic glycine concentration in relevant brain areas. It is also valuable to monitor patient compliance to prescribed doses of glycine.

Summary. MRS can monitor glycine in brain. MRS guided by SPECT scans has also been performed to obtain measurements in diseased brain regions. Others have used MRS to monitor brain glutamine, a marker of ammonia metabolism. This been done for inborn errors of metabolism and acquired disorders such as hepatic encephalopathy.

Detection and Measurement of Free Glycine in the Brain of an Individual Receiving High-Dose Glycine Treatment for Obsessive Compulsive Disorder and Co-morbidities. Successful treatment of psychiatric disorders with high-dose glycine requires that the dose be adjusted to give a therapeutic level of glycine in the regions of the brain that are abnormal. In all studies so far, the dose of ingested glycine has been determined by trial and error. It would be highly desirable to monitor directly the concentration of free glycine in the specific regions of the brain where abnormalities cause the psychiatric disorder.

One approach to the measurement of free glycine in brains of human patients with psychiatric disorders is magnetic resonance spectroscopy (MRS) that is guided by magnetic resonance imaging (MRI). In this procedure, magnetic resonance spectroscopy is used to measure the concentration of compounds whose peaks are resolvable in a cubical region of space (voxel) that is typically 2-3 cm on an edge. The positioning of the voxel relative to specific regions of the brain is guided by magnetic resonance imaging.

Figure 2:
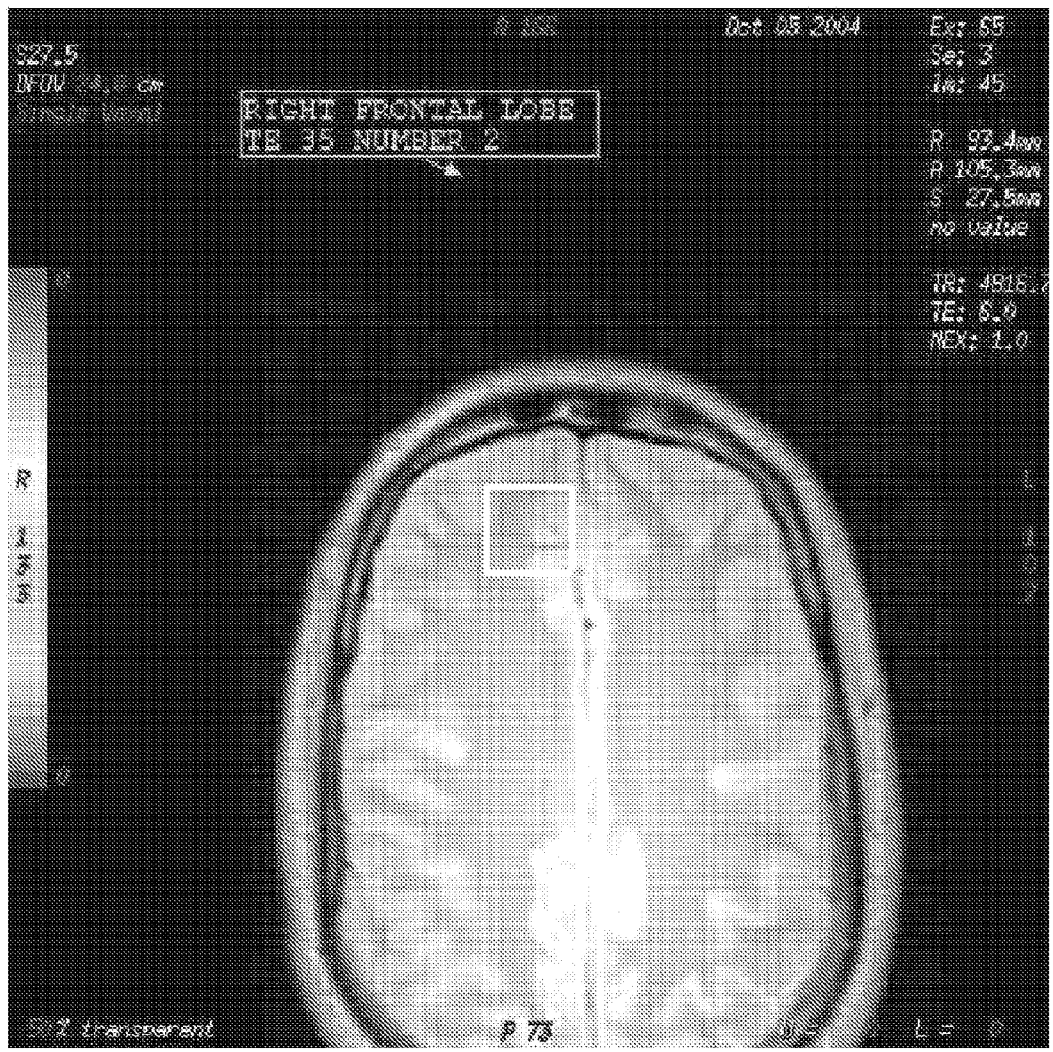
FIG. 2 depicts the brain scan of Subject 1 patient.

On Oct. 5, 2004, an attempt was made to measure the free glycine level in the right frontal lobe of an individual with obsessive-compulsive disorder (and co-morbidities) during a period in which glycine was consumed at high dose. FIG. 1 shows the magnetic resonance spectrum associated with the voxel shown in FIG. 2. The spectrum clearly shows a peak centered at 3.5 ppm, which is the expected position for a glycine peak as demonstrated previously (Sener, R. N., (2003) *Computerized Medical Imaging and Graphics* 27: 297-305). This represents an early report of the detection of free glycine in the brain of an individual receiving high-dose glycine. A spectrum of a normal individual obtained under comparable conditions has been published in the literature (Moore and Galloway, (2002) *Psychopharmacol Bulletin* 36(2): 5-23). It shows no detectable glycine peak. A recent paper in 2006, presented evidence that with a 4 Tesla magnet, a peak corresponding to free glycine could be detected in normal individuals (Prescot, el al. (2006) *Magnetic Resonance in Medicine,* 55(3): 681-686). This suggests that brain levels of free glycine will more become more easily measurable when more powerful MRI/MRS machines that are in preclinical development, become available in the clinic in the near future (Moore and Galloway, (2002) *Psychopharmacol Bulletin* 36(2): 5-23).

In the measurement described above, the decision to place the voxel in the right frontal lobe was not based on MRI data, since the latter revealed only a very minor structural abnormality (Virchow-Robin space) that would not be expected to cause a psychiatric disorder. Also, the MRS perfusion measurements were normal. Therefore, to position the voxel, an alternate procedure was developed that utilized information derived from Technetium-99m-HMPAO SPECT (SPECT) scans, which showed substantial abnormalities in regional cerebral blood flow, specifically hypoperfusion in regions relevant to obsessive compulsive disorder (and the patient's other co-morbidities). Four SPECT scans taken from 1999 to 2004 reproducibly revealed, "marked, heterogeneous and decreased cortical uptake [relative to cerebellum] throughout both cerebral hemispheres." In addition, "severe white matter hypoperfusion" was also noted. Clinical evaluation suggested no significant differences in the four scans. One of the scans was selected for a semiquantitative analysis, which revealed that the most severe hypoperfusion was observed in the right frontal lobe. This information guided the placement of the voxel for MRS described above. Previously, it has been noted that SPECT and also 18F-fluorodeoxyglucose PET scans can detect brain abnormalities in individuals with normal MRI and CT scans (Lin et al, (1997) *J Nuclear Medicine* 38(7): 1115-1120). However, such information has not been used to position voxels for MRS, either in general or for the specific purpose of glycine measurement.

In the individual studied in this case study, "Subject 1", treatment with high-dose glycine has caused elevated plasma ammonia that peaks about 2 hours after completion of glycine ingestion. For example, measurement of plasma ammonia about 2 hrs after completion of ingestion of 25 grams gave a value of 118 μM (reference range<47). Two days later plasma glycine concentration at the same time after ingestion of the same amount of glycine was 2480 μM, a value highly elevated in relation to the no-glycine values for this individual (163-268 μM). In another set of measurements done on blood samples drawn at the same time, a plasma glycine concentration of 2615 μM was seen after ingestion of 28.5 grams of glycine. The corresponding ammonia concentration was 136 μM. Although these levels are transient, the degree of elevation makes it desirable to bring them closer to normal levels.

Hyperammonemia is seen in several abnormal conditions, e.g. inborn errors of metabolism that affect the urea cycle, small bowel syndrome, and others. One established method to control hyperammonemia is to administer arginine (Bachmann et al., (2004) *Molec Gen Metab.* 81: S52-S57). To explore the possible use of arginine in the control of hyperammonemia produced by glycine treatment, arginine was consumed with glycine. When the MRI/MRS scan described above was done, 3 grams of arginine were consumed at approximately the same time that 25 grams of glycine were taken. Plasma amino acids and plasma ammonia were also measured 3 hours after completion of glycine consumption and 45 minutes before the MRI/MRS scan was begun. This is about 1 hour later than the measurements reported above. Therefore, the glycine value is somewhat lower as expected on the basis of the measured half-life of glycine that results from the destruction of glycine by the glycine cleavage reaction and the citric acid cycle (Hahn and Sandfeldt, (1999) *Scan J Nephrol* 33: 222-227). Measurement of plasma ammonia yielded a value of 29 μM well within the reference range of 11-35 μM. Plasma glycine at this time was 1326 μM and considerably above the reference range (151-490). Arginine was 98 μM and within the reference range (15-128). It should be noted that this ammonia value was lower than any other recorded for this individual, including values obtained without glycine treatment. It thus appears that arginine combined with glycine is an effective treatment for the plasma hyperammonemia caused by high-dose glycine treatment in some individuals. It should also be noted that other techniques used to control hyperammonemia in known illnesses could also be employed during high-dose glycine treatment.

Control of plasma hyperammonemia is an important step in the prevention of abnormally high levels of ammonia in the brain. However, it highly desirable to monitor ammonia in the brain itself to ensure that the glycine cleavage reaction and the citric acid cycle in combination with the elevated brain glycine levels in the brain do not produce too much ammonia for the ammonia elimination processes of the brain. Since the brain has no urea cycle, brain ammonia is eliminated by reaction with glutamate to produce glutamine, which is transported out of the brain. Inadequate control of ammonia elimination is thought to lead to elevated concentration of brain glutamine. Excess brain ammonia levels from high-dose glycine treatment could therefore be monitored by measuring the combined peak of glutamate+glutamine with MRS, as shown in the MRS data (FIG. 1) and shown in the literature for other illnesses that involve hyperammonemia, such as hepatic encephalopathy (Grover et al., (2006) *World J Gastroenterology,* 12(19): 2969-2978) and ornithine carbamoyl transferase deficiency (Connelly et. al., (1993) *Pediatric Research* 33(1): 77-81).

The monitoring techniques described above are expected to be of great use in high-dose glycine therapy by making it possible to determine the correct dose of glycine needed to ensure a therapeutic level in the brain, to ensure that patients reliably take the prescribed dose, and to ensure that toxic levels of ammonia are not being produced in the brain. In addition, these techniques will facilitate much more rigorous clinical trials of high-dose glycine for any illness involving the brain for which it might be therapeutic.

Example 3

Effects of High-Dose Glycine Treatment on Cognition in an Individual with Diagnoses of Obsessive Compulsive Disorder, Body Dysmorphic Disorder, and, as attention Deficit Disorder In addition to obsessive-compulsive disorder and body dysmorphic disorder, cognition difficulties represent another dimension of Subject 1's illness that has caused significant distress. Given the large body of literature on the effects of NMDA receptor co-agonists on learning and memory (see for example: Coyle and Tsai, (2000) *Psychopharmacology* 174: 32-38.), it is of interest to consider the effects of high-dose glycine therapy on cognition in Subject 1, who has diagnoses of Obsessive Compulsive Disorder, Body Dysmorphic Disorder, and, as discussed below, Attention Deficit Disorder. The very detailed history that is available provides sufficient objective evidence for a cognitive evaluation. Available evidence consists of records for formal cognitive testing at age 7, school records from pre-kindergarten through college (in progress), SAT scores, including scores on practice tests in an SAT preparation course, and diary-recorded observations made in parental tutoring sessions occurring from first grade through college.

Psychological evaluation of Subject 1 at age 7 was requested by his school on the basis of poor academic performance in the first grade. Testing revealed multiple signs of cognition difficulties that, in conjunction with behavioral signs, prompted a diagnosis of Attention Deficit Disorder (ADD). It should be noted that ADD (or Attention Deficit/Hyperactivity Disorder (ADHD)) is not uncommon as a co-morbidity of obsessive-compulsive disorder. For example, the Swedo group has reported that 40% of patients with PANDAS, a subtype of OCD, meet DSM-IV (American Psychiatric Association, 1994) criteria for ADHD and/or Oppositional Defiant Disorder (Swedo and Grant, (2005) *J Child Psychol Psych,* 46(3): 227-234). In this context, it is of interest that cognition difficulties appear to have preceded the emergence of OCD and BDD, since a psychiatric evaluation at the time of testing did not reveal these disorders. Moreover, Subject 1's recollections of ritualistic behaviors (which were never noticed by parents until age 14) go back no further than fourth grade (age 10).

In eighth grade, Subject 1's father tutored him in mathematics in preparation for a standardized test required for admission to a competitive high school. He notes that repeated explanations of algebra topics were not retained. "You could explain something to him many times and it would not sink in." As an example of errors suggesting deficient attention and/or working memory, Subject 1's father recollects the occurrence of frequent copying errors in the course of doing a problem, especially incomplete copying of an algebraic expressions with multiple terms. Retrospective examination of the report for age 7 cognitive testing has revealed descriptions of similar errors. When prompted to take a second look at his work, Subject 1 would immediately note the error with an "Oh!". A similar phenomenon was noted in the report for the psychological examination done at age 7.

Subject 1's own recollections (in adulthood) also support difficulties pertaining to memory. For example, he recalls that in elementary school the meaning of a word found in a dictionary would be forgotten as soon as the dictionary was closed.

Objective measurements of cognition during periods of sustained glycine treatment are available in the form of SAT test scores and test grades in college courses. Preparation for the SAT test included a test preparation course that involved practice tests that simulated actual test conditions. During this course, scores on both math and verbal practice tests climbed significantly. The math scores for tests 1-3 were 390, 460, and 490, respectively. The verbal scores were 540, 540, and 600, respectively. The math score for the official test was 520. The verbal score in the official test was 660, a score in the 90$^{th}$ percentile. It should be noted that both official and unofficial SAT tests were taken in the standard time intervals. The substantial improvement seen from the first practice tests to the final, official tests suggests a general cognition competence with both good working memory and memory retrieval, including memory retrieval under stress (Roozendaal, (2002) *Neurobiol of Learning and Memory* 78: 578-595). It should be kept in mind that Subject 1 completed less than two years of high school as a result of the emergence of highly impairing OCD and BDD symptoms in the first year of high school at age 15. The remainder of his high school education consisted of self-study and parental tutoring that led to a GED degree at age 25. Subject 1's father reports that psychiatric impairment prevented all but intermittent self-study and parental tutoring during this 10-year period. After the initiation of high-dose glycine treatment at age 25 and 4 months, receptivity to parental tutoring improved substantially and self-study became more systematic as a result of studying in a library on a 9 AM-5 PM weekday schedule. The GED test was passed 5 months later on the first attempt.

Objective evidence for a cognitive decline following cessation of glycine consumption can be seen in algebra tests given in Subject 1's first semester of college. After taking glycine at a moderately high dose (for the previous three months, average daily dose=37.4 grams), glycine was stopped in early January 2004 (Jan. 10, 2004). At this time, Subject 1's father observed rapid absorption of algebra topics in tutoring sessions for a mathematics placement test given on the occasion of entrance into college at age 26 (Jan. 22, 2004). The score that was obtained qualified Subject 1 for a pre-calculus course. However, he chose to take a course one level lower since he not taken a course at that level as a result of missing much of high school. Tests in this course taken 10 and 14 weeks after glycine cessation were given scores in the low 90% range. No parental tutoring was given and it should be noted that Subject 1 received no special accommodations in this course.

Signs of a relapse appeared in tests taken at 21 and 26 weeks after glycine cessation. Scores were in the low 80% range. After the first low score, Subject 1's father initiated tutoring and examined the errors made on exams. The deficient attention and working memory seen in eighth grade was again apparent. Specific examples suggesting such defects were recorded at this time by Subject 1's father. For example, when asked to calculate 1/(b−a), Subject 1 calculated b−a and gave the result as the answer, i.e. in the course of calculating b−a, he appeared to have forgotten that he had been asked for the reciprocal of b−a. It is of interest that this type of error was noted in the report on cognitive testing done at age 7. Subject 1's father also reports that the tendency to make errors in copying algebraic expressions from one line to another or in substitution steps again became quite noticeable, as they had been in the eighth grade. These errors suggest a decline in working memory and/or attention that emerged approximately 5 months after glycine cessation.

With intensive tutoring, Subject 1's grades improved. Due to Subject 1's reluctance, glycine was not resumed until the last three weeks of the course and then at less than one-half (average daily dose=19.4 grams/day) of the normal dose (40-60 grams/day).

Additional evidence for cognitive decline following glycine cessation was obtained in recent parental tutoring sessions for an undergraduate course in molecular biology. At age 29, and about 6 months after glycine cessation, Subject 1's father noted that many, repetitive explanations over several days were needed before Subject 1 could reliably give correct answers for the numbers of H-bonds in AT and GC base pairs. In the course of these explanations, the importance of these facts was strongly emphasized. One and a half months after the course was over, Subject 1 was again queried by his father on this topic. He remembered that AT has two H-bonds but did not remember that GC has three. This example, occurring nine months after glycine cessation, provides evidence of a return of difficulties in memory consolidation and/or retrieval, even when simple concepts are involved.

The above observations suggest that cognition improved in response to high-dose glycine treatment and declined on two occasions after cessation of glycine treatment. More specifically, these observations suggest that high-dose glycine treatment can improve working memory and attention as well as memory consolidation in an individual with diagnoses of obsessive-compulsive disorder, body dysmorphic disorder and attention deficit disorder. These observations therefore generate motivation for more systematic studies that combine cognitive testing with MRI and measure cognitive abilities as a function of the level of brain glycine as measured by MRS.

What is claimed:

1. A method for treating a subject having at least one obsessive-compulsive spectrum disorder, the method comprising administering to the subject a therapeutic amount of a composition, comprising:
(i) an agonist of at least one N-methyl-D-aspartate receptor (NMDAR) having the structure:

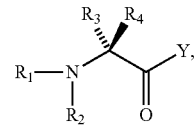

wherein $R_1$ or $R_2$ is —H, —$CH_3$, —$C_1$-$C_6$ alkyl, —$C_2$-$C_6$ alkyl, —$C_2$-$C_6$ alkenyl, —$C_2$-$C_6$ alkynyl, -aryl, —($C_1$-$C_6$ alkyl)-aryl, —$C_3$-$C_6$ alkyl, $C_2$-$C_4$ alkyl, —$OR_5$, —CN, —$CF_3$, —$OCF_3$, —$NO_2$, —$NH_2$, —NH($C_1$-$C_6$ alkyl), —N($C_1$-$C_6$ alkyl)$_2$, —NHC(O)—($C_1$-$C_6$ alkyl), —NHC(O)NH($C_1$-$C_6$ alkyl), —$SO_2NH_2$, —$SO_2$NH ($C_1$-$C_6$ alkyl), —$SO_2$N($C_1$-$C_6$ alkyl)$_2$, —NHSO($C_1$-$C_6$ alkyl), —C(O)O—($C_1$-$C_6$ alkyl), —C(O)NH($C_1$-$C_6$ alkyl), or —C(O)N($C_1$-$C_6$ alkyl)$_2$;

$R_3$ or $R_4$ is —H, —$C_1$-$C_6$ alkyl, —$C_2$-$C_6$ alkenyl, —$C_2$-$C_6$ alkynyl, -aryl, —$CH_2$—O—$R_5$, —$CH_2$—$R_5$, —($C_1$-$C_6$ alkyl)- aryl, -5 or 6-membered aromatic or non-aromatic heterocycle or —($C_1$-$C_6$ alkyl)-(5 or 6-membered aromatic or non-aromatic heterocycle), wherein the —$C_1$-$C_6$ alkyl, —$C_2$-$C_6$ alkenyl, —$C_2$-$C_6$ alkynyl, -aryl, —(C$_1$-C$_6$ alkyl)-aryl, -5 or 6-membered aromatic or non-aromatic heterocycle or —(C$_1$-C$_6$ alkyl)-(5 or 6-membered aromatic or non-aromatic heterocycle) group is unsubstituted or substituted with at least one of the following groups: -halo, —OR$_5$, —CN, —C$_1$-C$_6$ alkyl, —C$_2$-C$_6$ alkenyl, —C$_2$-C$_6$ alkynyl, —CF$_3$, —OCF$_3$, —NO$_2$, —NH$_2$, —NH(C$_1$-C$_6$ alkyl), —N(C$_1$-C$_6$ alkyl)$_2$, —NHC(O)—(C$_1$-C$_6$ alkyl), —NHC(O)NH(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —NHSO(C$_1$-C$_6$ alkyl), —C(O)O—(C$_1$-C$_6$ alkyl), —C(O)NH(C$_1$-C$_6$ alkyl), or —C(O)N(C$_1$-C$_6$ alkyl)$_2$;

Y is -halo, —OR$_5$, —CN, —C$_1$-C$_6$ alkyl, —C$_2$-C$_6$ alkenyl, —C$_2$-C$_6$ alkynyl, -aryl, —(C$_1$-C$_6$—CF$_3$, —OCF$_3$, —NO$_2$, —NH$_2$, —NHC$_1$-C$_6$ alkyl), —N(C$_1$-C$_6$ alkyl)$_2$, or —NHNH—R$_5$; and R$_5$=R$_1$ or R$_3$; and (ii) a carrier;

wherein the therapeutic amount is effective to reduce at least one obsessive-compulsive spectrum disorder (OCSD) behavior by the subject relative to a control subject who has not been treated with the composition, and the obsessive-compulsive spectrum disorder (OCSD) behavior is selected from the group consisting of a social discomfort behavior, a mirror intolerance behavior, a perseverative behavior, a line-crossing obsession, a prayer ritual, a hand washing ritual, or a combination thereof.

2. The method according to claim 1, wherein the at least one obsessive-compulsive spectrum disorder is selected from the group consisting of a body dysmorphic disorder, a compulsive skin picking, an attention deficit/hyperactivity disorder, a torticollis, an anorexia nervosa, an antisocial personality disorder (ASPD), an autism, a basal ganglia disorder, a borderline personality disorder (BPD), a bulimia, a depersonalization disorder, an epilepsy, a hypochondriasis, a kleptomania, a personality disorder, a pathologic gambling disorder, and a sexual compulsion.

3. The method according to claim 1, wherein the at least one obsessive-compulsive spectrum disorder is Tourette syndrome.

4. The method according to claim 1, wherein the at least one obsessive-compulsive spectrum disorder is Huntington's disease.

5. The method according to claim 1, wherein the agonist of the N-methyl-D-aspartate receptor (NMDAR) is selected from the group consisting of glycine, serine, alanine, cycloserine, or a derivative thereof.

6. The method according to claim 5, wherein the agonist of the N-methyl-D-aspartate receptor (NMDAR) is glycine administered at a dose of at least about 0.05 g/kg/body weight/day to at least about 1.5 g/kg body weight/day.

7. The method according to claim 1, wherein the carrier is a palatable edible matrix.

8. The method according to claim 1, wherein the administering step occurs via subcutaneous injection, intra-muscular injection, intra-peritoneal injection, intravenous injection; infusion; oral delivery, nasal delivery, topical delivery, or a combination thereof.

9. The method according to claim 1, wherein the composition further comprises a glycine transporter inhibitor.

10. The method according to claim 1, wherein the composition further comprises at least one additional therapeutic agent.

11. The method according to claim 1, wherein the agonist of the N-methyl-D-aspartate receptor (NMDAR) is glycine having the structure:

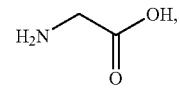

12. The method according to claim 9, wherein the glycine transporter inhibitor is selected from the group consisting of sarcosine, glycylodecylamide, N[3-(4'-fluorophenyl)-3-(4'-phenylphenoxy)propyl]sarcosine, Organon-24461, Organon-24598, R-NPTS, SSR5044734, or a derivative thereof.

13. The method according to claim 12, wherein the glycine transporter inhibitor is sarcosine.

14. The method according to claim 10, wherein the additional therapeutic agent is selected from the group consisting of an atypical antipsychotic, a typical antipsychotic, an anti-androgen, an anticonvulsant and an antidepressant.

15. The method according to claim 10, wherein the additional therapeutic agent is L-arginine.

16. The method according to claim 15, wherein the at least one additional therapeutic is L-arginine administered at a dose of at least about 0.04 g/kg body weight/day.

17. The method according to claim 1, wherein the obsessive-compulsive spectrum disorder (OCSD) behavior is a social discomfort behavior.

18. The method according to claim 17, wherein the therapeutic amount is effective to decrease social discomfort.

19. The method according to claim 1, wherein the obsessive-compulsive spectrum disorder (OCSD) behavior is a mirror intolerance behavior.

20. The method according to claim 1, wherein the obsessive-compulsive spectrum disorder (OCSD) behavior is a perseverative behavior.

21. The method according to claim 12, wherein the obsessive-compulsive spectrum disorder (OCSD) behavior is a line-crossing obsession.

22. The method according to claim 12, wherein the obsessive-compulsive spectrum disorder (OCSD) behavior is a prayer ritual.

23. The method according to claim 12, wherein the obsessive-compulsive spectrum disorder (OCSD) behavior is a hand washing ritual.

24. The method according to claim 1, wherein the therapeutic amount is effective to treat a cognitive impairment.

* * * * *